(12) United States Patent
Inoue et al.

(10) Patent No.: US 9,793,498 B2
(45) Date of Patent: *Oct. 17, 2017

(54) ORGANOMETALLIC COMPLEX, AND LIGHT-EMITTING ELEMENT AND LIGHT-EMITTING DEVICE USING THE SAME

(71) Applicant: Semiconductor Energy Laboratory Co., Ltd., Atsugi-shi, Kanagawa-ken (JP)

(72) Inventors: Hideko Inoue, Atsugi (JP); Masakazu Egawa, Isehara (JP); Satoshi Seo, Kawasaki (JP)

(73) Assignee: Semiconductor Energy Laboratory Co., Ltd., Kanagawa-ken (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/184,197

(22) Filed: Jun. 16, 2016

(65) Prior Publication Data

US 2016/0293867 A1 Oct. 6, 2016

Related U.S. Application Data

(63) Continuation of application No. 14/706,270, filed on May 7, 2015, now Pat. No. 9,373,799, which is a continuation of application No. 12/894,953, filed on Sep. 30, 2010, now Pat. No. 9,048,441, which is a continuation of application No. 11/527,449, filed on Sep. 27, 2006, now Pat. No. 7,807,839.

(30) Foreign Application Priority Data

Oct. 18, 2005 (JP) .................................. 2005-303730

(51) Int. Cl.
*H01L 51/54* (2006.01)
*C09K 11/06* (2006.01)
(Continued)

(52) U.S. Cl.
CPC ...... *H01L 51/0085* (2013.01); *C07F 15/0033* (2013.01); *C07F 15/0046* (2013.01); *C09K 11/06* (2013.01); *H01L 51/008* (2013.01); *H01L 51/009* (2013.01); *C09K 2211/1007* (2013.01); *C09K 2211/1022* (2013.01); *C09K 2211/1048* (2013.01); *C09K 2211/1059* (2013.01); *C09K 2211/185* (2013.01); *H01L 27/3211* (2013.01);
(Continued)

(58) Field of Classification Search
None
See application file for complete search history.

(56) References Cited

U.S. PATENT DOCUMENTS 5,484,922 A * 1/1996 Moore et al. .......... H05B 33/14
 313/503
6,821,645 B2 11/2004 Igarashi et al.
(Continued)

FOREIGN PATENT DOCUMENTS

| KR | 2004-0014346 A | 2/2004 |
| WO | WO-2004/101707 | 11/2004 |
| WO | WO-2006/000544 | 1/2006 |

OTHER PUBLICATIONS

Baldo et al., "Very High-Efficiency Green Organic Light-Emitting Devices Based on Electrophosphorescence", Appl. Phys. Lett. (Applied Physics Letters), Jul. 5, 1999, vol. 75, No. 1, pp. 4-6.
Chen et al., "Synthesis, structure, electrochemistry, photophysics and electroluminescence of 1,3,4-oxadiazole-based ortho-metalated iridium(III) complexes", Journal of Organometallic Chemistry, Aug. 1, 2006, vol. 691, No. 16, pp. 3519-3530.
(Continued)

*Primary Examiner* — Marie R. Yamnitzky
(74) *Attorney, Agent, or Firm* — Robinson Intellectual Property Law Office; Eric J. Robinson

(57) ABSTRACT

It is an object of the present invention to provide an organometallic complex that can emit phosphorescence. In the following general formula (G1), X represents —O— or —N($R^{10}$)—. $R^1$ to $R^9$ each represent any of hydrogen, an alkyl group or a cycloalkyl group having 1 to 6 carbon atoms, an alkoxy group having 1 to 6 carbon atoms, an alkoxycarbonyl group having 1 to 6 carbon atoms, an acyl group having 1 to 6 carbon atoms, an acyloxy group having 1 to 6 carbon atoms, a halogen group, a haloalkyl group, and an aryl group having 6 to 12 carbon atoms. In addition, $R^{10}$ represents any of an alkyl group or a cycloalkyl group having 1 to 6 carbon atoms, an acyl group having 1 to 6 carbon atoms, an aryl group having 6 to 12 carbon atoms, and a heteroaryl group having 4 to 10 carbon atoms. Moreover, M represents an element belonging to Group 9 or 10.

(G1)

14 Claims, 13 Drawing Sheets

(51) Int. Cl.
  *H01L 51/00* (2006.01)
  *C07F 15/00* (2006.01)
  H01L 51/50 (2006.01)
  H01L 27/32 (2006.01)
  H01L 51/52 (2006.01)

(52) U.S. Cl.
  CPC ...... *H01L 27/3244* (2013.01); *H01L 51/0087* (2013.01); *H01L 51/5016* (2013.01); *H01L 51/5056* (2013.01); *H01L 51/5203* (2013.01)

(56) References Cited

U.S. PATENT DOCUMENTS

| | | | |
|---|---|---|---|
| 7,566,505 | B2 | 7/2009 | Ise et al. |
| 7,667,228 | B2 | 2/2010 | Okuda et al. |
| 7,807,839 | B2 | 10/2010 | Inoue et al. |
| 8,106,390 | B2 | 1/2012 | Okuda et al. |
| 8,178,874 | B2 | 5/2012 | Okuda et al. |
| 9,048,441 | B2 | 6/2015 | Inoue et al. |
| 9,373,799 | B2 * | 6/2016 | Inoue et al. ........ C07F 15/0046 |
| 2004/0026663 | A1 | 2/2004 | Heuer et al. |
| 2005/0064238 | A1 | 3/2005 | Lee et al. |
| 2006/0008670 | A1 | 1/2006 | Lin et al. |
| 2006/0036097 | A1 | 2/2006 | Qiu et al. |
| 2006/0134461 | A1 | 6/2006 | Huo et al. |
| 2006/0154106 | A1 | 7/2006 | Walters et al. |
| 2009/0102370 | A1 | 4/2009 | Taka et al. |
| 2012/0169219 | A1 | 7/2012 | Okuda et al. |

OTHER PUBLICATIONS

Zamora et al., "Synthesis of Several palladium Complexes Derived from 2,5-diphenyl-1,3,4-Oxadiazole. Reactivity against Nucleobase models", Journal of Inorganic Biochemistry, Dec. 1, 1997, vol. 68, No. 4, pp. 257-263.

Liu et al., "Green-Yellow Electrophosphorescence from di [2,5-diphenyl-1,3,4-oxadiazole C2', N3] Platinum(II) Doped PVK Devices", Chin. Phys. Lett. (Chinese Physics Letters), 2005, vol. 22, No. 3, pp. 723-726.

Wu et al., "Synthesis and photoluminescence of a novel iridium complex(BuPhOXD)2lr(acac)with unit of 1,3,4-oxadiazole", Chinese Chemical letters, 2005, vol. 16, No. 2, pp. 241-244, Chinese Chemical Society, (abstract only).

Search Report (Application No. 06021150.5) Dated Jan. 29, 2007.

van Diemen et al., "Synthesis and Characterization of Orthometalated Rhodium (III) Complexes Containing Substituted Triazoles", Inorganic Chemistry, 1991, vol. 30, No. 21, pp. 4038-4043, American Chemical Society.

Holder et al., "New Trends in the Use of Transition Metal-Ligand Complexes for Applications in Electroluminescent Devices", Adv. Mater. (Advanced Materials), May 1, 2005, vol. 17, No. 9, pp. 1109-1121.

Korean Office Action (Application No. 2011-0105518) Dated Jan. 15, 2013.

Holmes et al., "Efficient Deep-Bule Organic Electrophosphorescence by Guest Charge Trapping", Appl. Phys. Lett. (Applied Physics Letters), Nov. 3, 2003, vol. 83, No. 18, pp. 3818-3820.

* cited by examiner

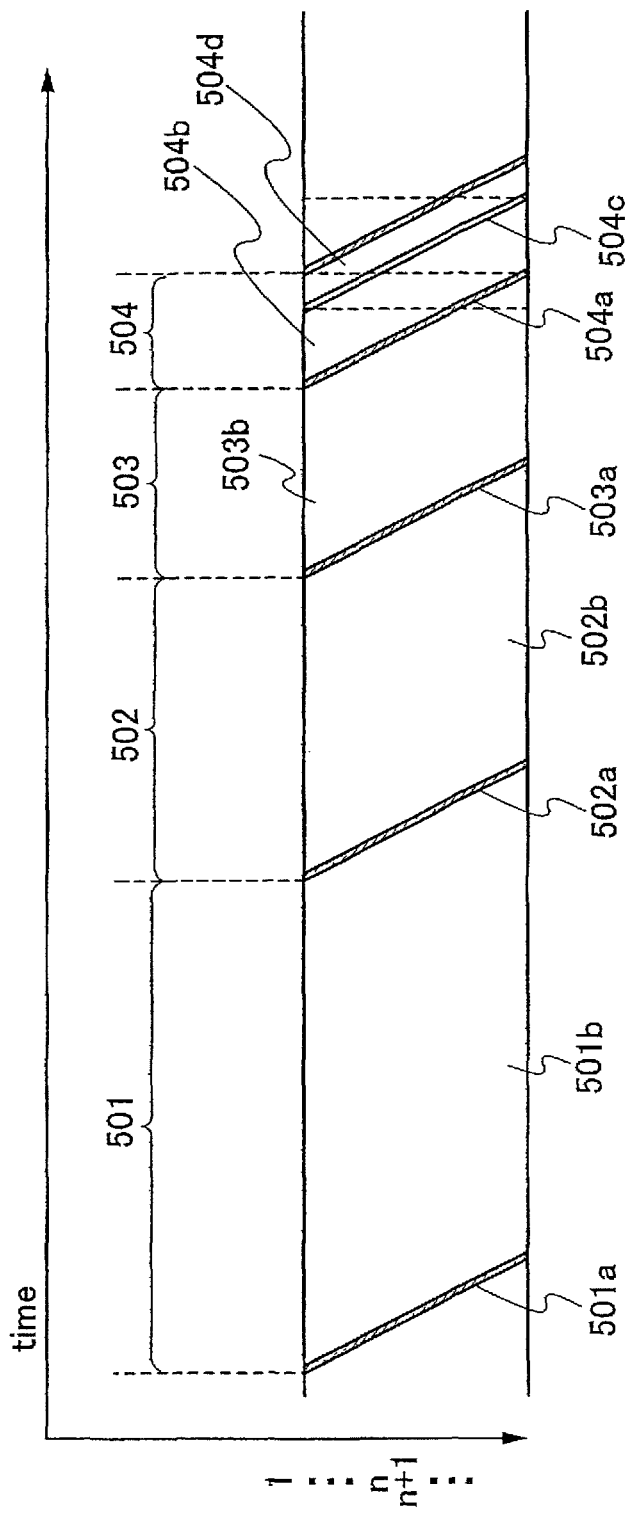

ORGANOMETALLIC COMPLEX, AND LIGHT-EMITTING ELEMENT AND LIGHT-EMITTING DEVICE USING THE SAME

BACKGROUND OF THE INVENTION

1. Field of the Invention

The present invention relates to a substance that can emit light by current excitation. In particular, the present invention relates to a substance that can obtain light emission from a triplet excited state. In addition, the present invention relates to a light-emitting element and a light-emitting device using the substance.

2. Description of the Related Art

A light-emitting element using an organic compound has characteristics such as a thin shape and lightweight, and high-speed response. Additionally, the light-emitting element is self-light emitting element. Therefore, a display device using the light-emitting element for a pixel portion has been actively developed in recent years.

A light-emission mechanism of the light-emitting element is said as follows. By applying a voltage by sandwiching a light-emitting layer between a pair of electrodes, electrons injected from a cathode and holes injected from an anode are recombined at a light-emission center of the light-emitting layer to form a molecular exciton, and energy is released from the molecular exciton in returning to a ground state, thereby emitting light. A singlet-excited state and a triplet-excited state are known as an excited state, and it is considered that light emission is possible through either excited state.

In such a light-emitting element, since more of triplet-excited states are generated than a single-excited state, luminous efficiency of the light-emitting element can be increased by using a material that can emit light from a triplet-excited state (a phosphorescent material). Therefore, it has been attempted number of times so far to use a phosphorescent material for a light-emitting element.

There is a metal complex, where iridium (Ir) is the central metal (hereinafter, referred to as an Ir complex), as a typical phosphorescent material which emits green light (for example, see Reference 1: M. A. Baldo and four others, Applied Physics Letters, Vol. 75, No. 1, p. 4). In Reference 1, green light emission is obtained by dispersing the Ir complex, where 2-phenylpyridine is a ligand, into a host material.

However, most of the phosphorescent materials generally emit light having a comparatively long wavelength such as red or orange light, and there are a few reports of a phosphorescent material that emits green or blue light so far. As for an Ir complex where 2-phenylpyridine and a derivative thereof are ligands, it is known that light having a wavelength band of green to blue is emitted. However, there is a property that holes are likely to be injected, whereas electrons are unlikely to be injected; therefore, an element structure thereof is limited in a case of applying the Ir complex to a light-emitting element. Moreover, there is also a problem that the Ir complex is poor in heat resistance, which can be said for the overall organometallic complexes.

Therefore, in the case of applying a phosphorescent material to a light-emitting element, it has been required to develop various phosphorescent materials which emit light having a wavelength band of green to blue so that the phosphorescent material can respond to a combination with various peripheral materials such as a host material, a hole-transporting material, and an electron-transporting material. In addition, it has been required to develop a phosphorescent material of green light or blue light having high heat resistance.

SUMMARY OF THE INVENTION

In view of the above problems, it is an object of the present invention to provide a novel substance that can emit phosphorescence. In particular, it is an object of the present invention to provide a novel substance that emits phosphorescence having a wavelength band of green to blue. In addition, it is another object of the present invention to provide a novel substance that emits phosphorescence and that is superior in heat resistance.

Moreover, it is another object of the present invention to provide a high-efficient light-emitting element that emits light having a wavelength band of green to blue by using such a novel substance. Further, it is another object of the present invention to provide a light-emitting device using the light-emitting element.

The present inventors found that an orthometalated complex where a 3,5-diphenyl-1,2,4-triazole complex is a ligand emits phosphorescence having a wavelength band of green to blue. In addition, the inventors also found that an orthometalated complex where a 2,5-diphenyl-1,3,4-oxadiazole derivative is a ligand emits phosphorescence having a wavelength band of green to blue.

One aspect of the present invention is an organometallic complex having a structure represented by a general formula (G1).

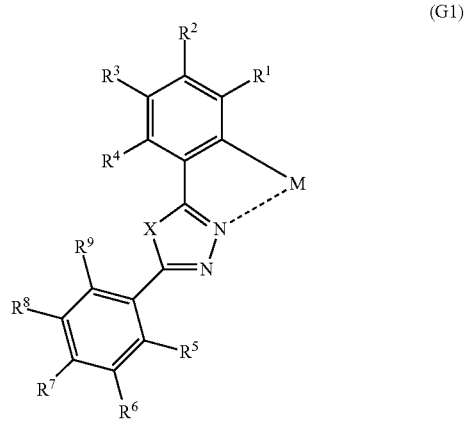

(G1)

In the general formula (G1), X represents —O— or —N($R^{10}$)—. $R^1$ to $R^9$ each represent any of hydrogen, an alkyl group or a cycloalkyl group having 1 to 6 carbon atoms, an alkoxy group having 1 to 6 carbon atoms, an alkoxycarbonyl group having 1 to 6 carbon atoms, an acyl group having 1 to 6 carbon atoms, an acyloxy group having 1 to 6 carbon atoms, a halogen group, a haloalkyl group, and an aryl group having 6 to 12 carbon atoms. In addition, $R^{10}$ represents any of an alkyl group or a cycloalkyl group having 1 to 6 carbon atoms, an acyl group having 1 to 6 carbon atoms, an aryl group having 6 to 12 carbon atoms, and a heteroaryl group having 4 to 10 carbon atoms. Moreover, M represents an element belonging to Group 9 or 10. Here, a group of any of a methyl group, an ethyl group, an isopropyl group, and a tert-butyl group is particularly preferable for an alkyl group. In addition, a cyclohexyl group is preferable for a cycloalkyl group. Moreover, a methoxy group is particularly preferable for an alkoxy group. Further, a methoxycarbonyl group is preferable for an alkoxycarbonyl group. An acetyl group is preferable for an acyl group. An acetoxy group is preferable for an acyloxy group. A fluoro group is preferable for a halogen group. A trifluoromethyl group is preferable for a haloalkyl group. Still further, an aryl group may have a substituent, and any of a phenyl group, a phenyl group substituted for a fluoro group, and a phenyl group substituted for a trifluoromethyl group is particularly preferable for an aryl group. A heteroaryl group may have a substituent, and a pyridyl group is particularly preferable for a heteroaryl group. Furthermore, iridium is particularly preferable for the element belonging to Group 9, and platinum is particularly preferable for the element belonging to Group 10.

Note that, among the above substituents, a fluoro group and a trifluoromethyl group each have an advantageous effect of making light-emission wavelength into a short wavelength; therefore, these groups are appropriate particularly in the present invention. It is considered that the cause is that, by introducing such an electron-withdrawing substituent as a fluoro group or a trifluoromethyl group, energy of a HOMO level of an organometallic complex is stabilized. This is because the HOMO level of an organometallic complex is decreased, thereby increasing an energy gap due to the decrease.

Another aspect of the present invention is an organometallic complex represented by a general formula (G2).

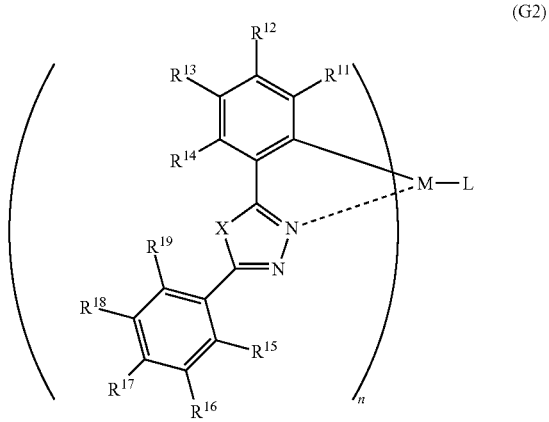

(G2)

In the general formula (G2), X represents —O— or —N(R$^{20}$)—. R$^{11}$ to R$^{19}$ each represent any of hydrogen, an alkyl group or a cycloalkyl group having 1 to 6 carbon atoms, an alkoxy group having 1 to 6 carbon atoms, an alkoxycarbonyl group having 1 to 6 carbon atoms, an acyl group having 1 to 6 carbon atoms, an acyloxy group having 1 to 6 carbon atoms, a halogen group, a haloalkyl group, and an aryl group having 6 to 12 carbon atoms. In addition, R$^{20}$ represents any of an alkyl group or a cycloalkyl group having 1 to 6 carbon atoms, an acyl group having 1 to 6 carbon atoms, an aryl group having 6 to 12 carbon atoms, and a heteroaryl group having 4 to 10 carbon atoms. Moreover, M represents an element belonging to Group 9 or 10. When M is an element belonging to Group 9, n=2, whereas, when M is an element belonging to Group 10, n=1. L represents a monoanionic bidentate ligand. Here, a group of any of a methyl group, an ethyl group, an isopropyl group, and a tert-butyl group is particularly preferable for an alkyl group. In addition, a cyclohexyl group is preferable for a cycloalkyl group. Moreover, a methoxy group is particularly preferable for an alkoxy group. Further, a methoxycarbonyl group is preferable for an alkoxycarbonyl group. An acetyl group is preferable for an acyl group. An acetoxy group is preferable for an acyloxy group. A fluoro group is preferable for a halogen group. A trifluoromethyl group is preferable for a haloalkyl group. Still further, an aryl group may have a substituent, and any of a phenyl group, a phenyl group substituted for a fluoro group, and a phenyl group substituted for a trifluoromethyl group is particularly preferable for an aryl group. A heteroaryl group may have a substituent, and a pyridyl group is particularly preferable for a heteroaryl group. Furthermore, iridium is particularly preferable for the element belonging to Group 9, and platinum is particularly preferable for the element belonging to Group 10. In addition, as a monoanionic bidentate ligand, any of a monoanionic bidentate ligand having a β-diketone structure, a monoanionic bidentate ligand having a carboxyl group, a monoanionic bidentate ligand having a phenolic hydroxyl group, and a monoanionic bidentate ligand where two ligand atoms are both nitrogen is preferable because of ease of synthesis.

Note that, among the above substituents, a fluoro group and a trifluoromethyl group each have an advantageous effect of making light-emission wavelength into a short wavelength; therefore, these groups are appropriate particularly in the present invention. It is considered that the cause is that, by introducing such an electron-withdrawing substituent as a fluoro group or a trifluoromethyl group, energy of a HOMO level of an organometallic complex is stabilized. This is because the HOMO level of an organometallic complex is decreased, thereby increasing an energy gap due to the decrease.

Another aspect of the present invention is an organometallic complex having a structure represented by a general formula (G3). Note that, as in the general formula (G3), from the perspective of luminous efficiency and heat resistance, iridium is preferable to platinum as the central metal.

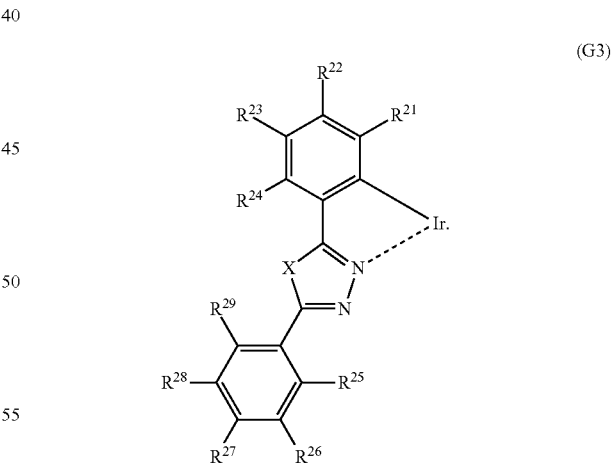

(G3)

In the general formula (G3), X represents —O— or —N(R$^{30}$)—. R$^{21}$ to R$^{29}$ each represent any of hydrogen, an alkyl group or a cycloalkyl group having 1 to 6 carbon atoms, an alkoxy group having 1 to 6 carbon atoms, an alkoxycarbonyl group having 1 to 6 carbon atoms, an acyl group having 1 to 6 carbon atoms, an acyloxy group having 1 to 6 carbon atoms, a halogen group, a haloalkyl group, and an aryl group having 6 to 12 carbon atoms. In addition, R$^{30}$ represents any of an alkyl group or a cycloalkyl group having 1 to 6 carbon atoms, an acyl group having to 6 carbon atoms, an aryl group having 6 to 12 carbon atoms, and a heteroaryl group having 4 to 10 carbon atoms. Here, a group of any of a methyl group, an ethyl group, an isopropyl group, and a tert-butyl group is particularly preferable for an alkyl group. In addition, a cyclohexyl group is preferable for a cycloalkyl group. Moreover, a methoxy group is particularly preferable for an alkoxy group. Further, a methoxycarbonyl group is preferable for an alkoxycarbonyl group. An acetyl group is preferable for an acyl group. An acetoxy group is preferable for an acyloxy group. A fluoro group is preferable for a halogen group. A trifluoromethyl group is preferable for a haloalkyl group. Still further, an aryl group may have a substituent, and any of a phenyl group, a phenyl group substituted for a fluoro group, and a phenyl group substituted for a trifluoromethyl group is particularly preferable for an aryl group. A heteroaryl group may have a substituent, and a pyridyl group is particularly preferable for a heteroaryl group.

Note that, among the above substituents, a fluoro group and a trifluoromethyl group each have an advantageous effect of making light-emission wavelength into a short wavelength; therefore, these groups are appropriate particularly in the present invention. It is considered that the cause is that, by introducing such an electron-withdrawing substituent as a fluoro group or a trifluoromethyl group, energy of a HOMO level of an organometallic complex is stabilized. This is because the HOMO level of an organometallic complex is decreased, thereby increasing an energy gap due to the decrease.

Another aspect of the present invention is an organometallic complex represented by a general formula (G4). Note that, as in the general formula (G4), from the perspective of luminous efficiency and heat resistance, iridium is preferable to platinum as the central metal.

Moreover, L represents a monoanionic bidentate ligand. Here, a group of any of a methyl group, an ethyl group, an isopropyl group, and a tert-butyl group is particularly preferable for an alkyl group. In addition, a cyclohexyl group is preferable for a cycloalkyl group. Moreover, a methoxy group is particularly preferable for an alkoxy group. Further, a methoxycarbonyl group is preferable for an alkoxycarbonyl group. An acetyl group is preferable for an acyl group. An acetoxy group is preferable for an acyloxy group. A fluoro group is preferable for a halogen group. A trifluoromethyl group is preferable for a haloalkyl group. Still further, an aryl group may have a substituent, and any of a phenyl group, a phenyl group substituted for a fluoro group, and a phenyl group substituted for a trifluoromethyl group is particularly preferable for an aryl group. A heteroaryl group may have a substituent, and a pyridyl group is particularly preferable for a heteroaryl group. In addition, for a monoanionic bidentate ligand, any of a monoanionic bidentate ligand having a β-diketone structure, a monoanionic bidentate ligand having a carboxyl group, a monoanionic bidentate ligand having a phenolic hydroxyl group, and a monoanionic bidentate ligand where two ligand atoms are both nitrogen is preferable because of ease of synthesis.

Note that, among the above substituents, a fluoro group and a trifluoromethyl group each have an advantageous effect of making light-emission wavelength into a short wavelength; therefore, these groups are appropriate particularly in the present invention. It is considered that the cause is that, by introducing such an electron-withdrawing substituent as a fluoro group or a trifluoromethyl group, energy of a HOMO level of an organometallic complex is stabilized. This is because the HOMO level of an organometallic complex is decreased, thereby increasing an energy gap due to the decrease.

In addition, in the organometallic complex represented by the general formula (G2) or (G4), it is preferable that L be a ligand represented by any of the following structural formulas (1) to (5).

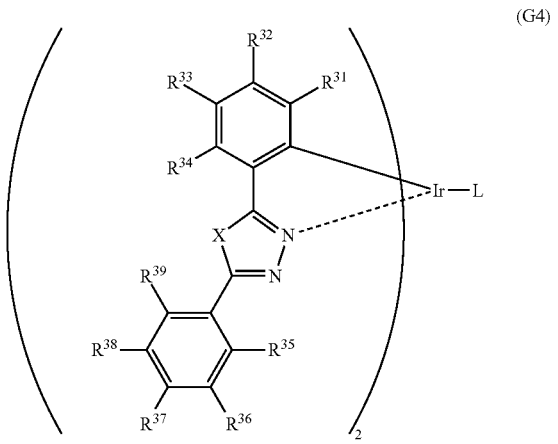

(G4)

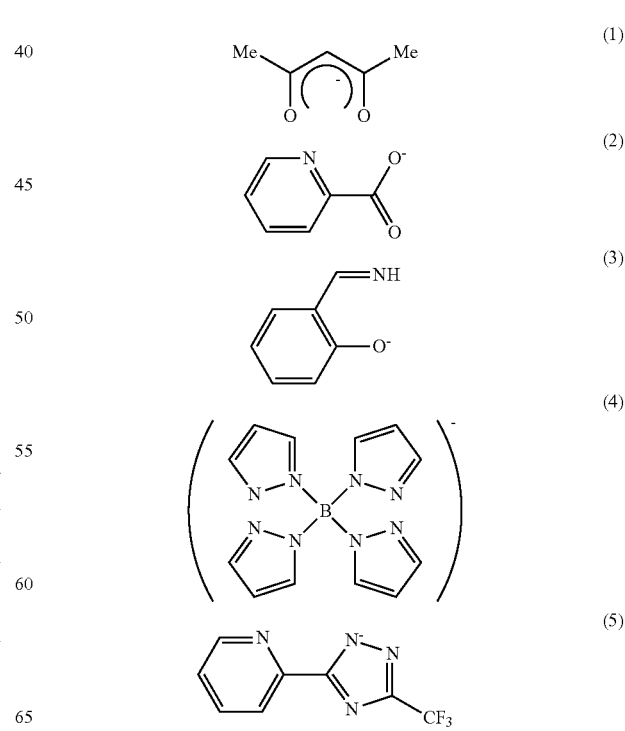

In the general formula (G4), X represents —O— or —N($R^{40}$)—. $R^{31}$ to $R^{39}$ each represent any of hydrogen, an alkyl group or a cycloalkyl group having 1 to 6 carbon atoms, an alkoxy group having 1 to 6 carbon atoms, an alkoxycarbonyl group having 1 to 6 carbon atoms, an acyl group having 1 to 6 carbon atoms, an acyloxy group having 1 to 6 carbon atoms, a halogen group, a haloalkyl group, and an aryl group having 6 to 12 carbon atoms. In addition, $R^{40}$ represents any of an alkyl group or a cycloalkyl group having 1 to 6 carbon atoms, an acyl group having 1 to 6 carbon atoms, an aryl group having 6 to 12 carbon atoms, and a heteroaryl group having 4 to 10 carbon atoms.

Another aspect of the present invention is an organometallic complex having a structure represented by a general formula (G5).

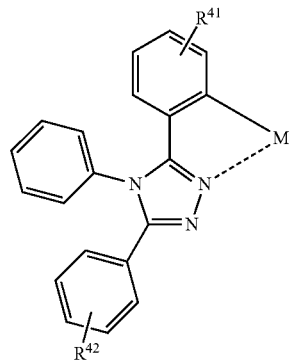

(G5)

In the general formula (G5), $R^{41}$ and $R^{42}$ each represent any of hydrogen, an alkyl group or a cycloalkyl group having 1 to 6 carbon atoms, an alkoxy group having 1 to 6 carbon atoms, an alkoxycarbonyl group having 1 to 6 carbon atoms, an acyl group having 1 to 6 carbon atoms, an acyloxy group having 1 to 6 carbon atoms, a halogen group, a haloalkyl group, and an aryl group having 6 to 12 carbon atoms. In addition, M represents an element belonging to Group 9 or 10. Here, a group of any of a methyl group, an ethyl group, an isopropyl group, and a tert-butyl group is particularly preferable for an alkyl group. In addition, a cyclohexyl group is preferable for a cycloalkyl group. Moreover, a methoxy group is particularly preferable for an alkoxy group. Further, a methoxycarbonyl group is preferable for an alkoxycarbonyl group. An acetyl group is preferable for an acyl group. An acetoxy group is preferable for an acyloxy group. A fluoro group is preferable for a halogen group. A trifluoromethyl group is preferable for a haloalkyl group. Still further, an aryl group may have a substituent, and any of a phenyl group, a phenyl group substituted for a fluoro group, and a phenyl group substituted for a trifluoromethyl group is particularly preferable for an aryl group. Furthermore, iridium is particularly preferable for the element belonging to Group 9, and platinum is particularly preferable for the element belonging to Group 10.

Note that, among the above substituents, a fluoro group and a trifluoromethyl group each have an advantageous effect of making light-emission wavelength into a short wavelength; therefore, these groups are appropriate particularly in the present invention. It is considered that the cause is that, by introducing such an electron-withdrawing substituent as a fluoro group or a trifluoromethyl group, energy of a HOMO level of an organometallic complex is stabilized. This is because the HOMO level of an organometallic complex is decreased, thereby increasing an energy gap due to the decrease.

Another aspect of the present invention is an organometallic complex represented by a general formula (G6).

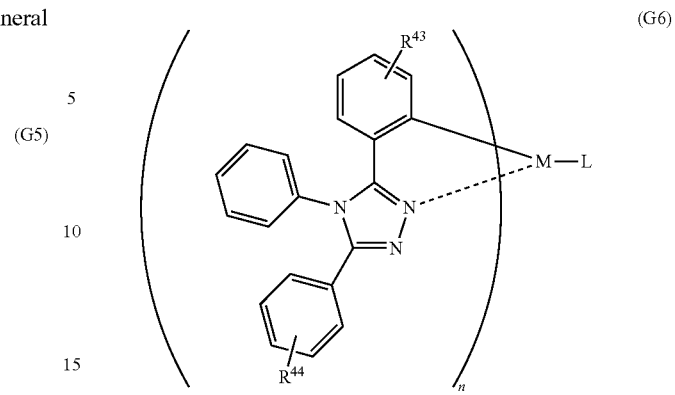

(G6)

In the general formula (G6), $R^{43}$ and e each represent any of hydrogen, an alkyl group or a cycloalkyl group having 1 to 6 carbon atoms, an alkoxy group having 1 to 6 carbon atoms, an alkoxycarbonyl group having 1 to 6 carbon atoms, an acyl group having 1 to 6 carbon atoms, an acyloxy group having 1 to 6 carbon atoms, a halogen group, a haloalkyl group, and an aryl group having 6 to 12 carbon atoms. In addition, M represents an element belonging to Group 9 or 10. When M is an element belonging to Group 9, n=2, whereas, when M is an element belonging to Group 10, n=1. L represents a monoanionic bidentate ligand. Here, a group of any of a methyl group, an ethyl group, an isopropyl group, and a tert-butyl group is particularly preferable for an alkyl group. In addition, a cyclohexyl group is preferable for a cycloalkyl group. Moreover, a methoxy group is particularly preferable for an alkoxy group. Further, a methoxycarbonyl group is preferable for an alkoxycarbonyl group. An acetyl group is preferable for an acyl group. An acetoxy group is preferable for an acyloxy group. A fluoro group is preferable for a halogen group. A trifluoromethyl group is preferable for a haloalkyl group. Still further, an aryl group may have a substituent, and any of a phenyl group, a phenyl group substituted for a fluoro group, and a phenyl group substituted for a trifluoromethyl group is particularly preferable for an aryl group. Furthermore, iridium is particularly preferable for the element belonging to Group 9, and platinum is particularly preferable for the element belonging to Group 10. In addition, as a monoanionic bidentate ligand, any of a monoanionic bidentate ligand having a β-diketone structure, a monoanionic bidentate ligand having a carboxyl group, a monoanionic bidentate ligand having a phenolic hydroxyl group, and a monoanionic bidentate ligand where two ligand atoms are both nitrogen is preferable because of ease of synthesis.

Note that, among the above substituents, a fluoro group and a trifluoromethyl group each have an advantageous effect of making light-emission wavelength into a short wavelength; therefore, these groups are appropriate particularly in the present invention. It is considered that the cause is that, by introducing such an electron-withdrawing substituent as a fluoro group or a trifluoromethyl group, energy of a HOMO level of an organometallic complex is stabilized. This is because the HOMO level of an organometallic complex is decreased, thereby increasing an energy gap due to the decrease.

Another aspect of the present invention is an organometallic complex having a structure represented by a general formula (G7). Note that, as in the general formula (G7), from the perspective of luminous efficiency and heat resistance, iridium is preferable to platinum as the central metal.

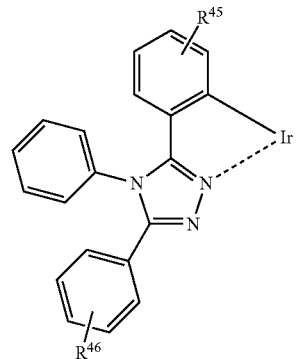

(G7)

In the general formula (G7), $R^{45}$ to $R^{46}$ each represent any of hydrogen, an alkyl group or a cycloalkyl group having 1 to 6 carbon atoms, an alkoxy group having 1 to 6 carbon atoms, an alkoxycarbonyl group having 1 to 6 carbon atoms, an acyl group having 1 to 6 carbon atoms, an acyloxy group having 1 to 6 carbon atoms, a halogen group, a haloalkyl group, and an aryl group having 6 to 12 carbon atoms. Here, a group of any of a methyl group, an ethyl group, an isopropyl group, and a tert-butyl group is particularly preferable for an alkyl group. In addition, a cyclohexyl group is preferable for a cycloalkyl group. Moreover, a methoxy group is particularly preferable for an alkoxy group. Further, a methoxycarbonyl group is preferable for an alkoxycarbonyl group. An acetyl group is preferable for an acyl group. An acetoxy group is preferable for an acyloxy group. A fluoro group is preferable for a halogen group. A trifluoromethyl group is preferable for a haloalkyl group. Still further, an aryl group may have a substituent, and any of a phenyl group, a phenyl group substituted for a fluoro group, and a phenyl group substituted for a trifluoromethyl group is particularly preferable for an aryl group.

Note that, among the above substituents, a fluoro group and a trifluoromethyl group each have an advantageous effect of making light-emission wavelength into a short wavelength; therefore, these groups are appropriate particularly in the present invention. It is considered that the cause is that, by introducing such an electron-withdrawing substituent as a fluoro group or a trifluoromethyl group, energy of a HOMO level of an organometallic complex is stabilized. This is because the HOMO level of an organometallic complex is decreased, thereby increasing an energy gap due to the decrease.

Another aspect of the present invention is an organometallic complex represented by a general formula (G8). Note that, as in the general formula (G8), from the perspective of luminous efficiency and heat resistance, iridium is preferable to platinum as the central metal.

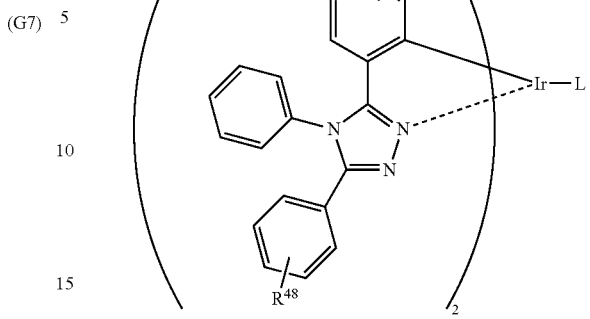

(G8)

In the general formula (G8), $R^{47}$ and $R^{48}$ each represent any of hydrogen, an alkyl group or a cycloalkyl group having 1 to 6 carbon atoms, an alkoxy group having 1 to 6 carbon atoms, an alkoxycarbonyl group having 1 to 6 carbon atoms, an acyl group having 1 to 6 carbon atoms, an acyloxy group having 1 to 6 carbon atoms, a halogen group, a haloalkyl group, and an aryl group having 6 to 12 carbon atoms. In addition, L represents a monoanionic bidentate ligand. Here, a group of any of a methyl group, an ethyl group, an isopropyl group, and a tert-butyl group is particularly preferable for an alkyl group. In addition, a cyclohexyl group is preferable for a cycloalkyl group. Moreover, a methoxy group is particularly preferable for an alkoxy group. Further, a methoxycarbonyl group is preferable for an alkoxycarbonyl group. An acetyl group is preferable for an acyl group. An acetoxy group is preferable for an acyloxy group. A fluoro group is preferable for a halogen group. A trifluoromethyl group is preferable for a haloalkyl group. Still further, an aryl group may have a substituent, and any of a phenyl group, a phenyl group substituted for a fluoro group, and a phenyl group substituted for a trifluoromethyl group is particularly preferable for an aryl group. In addition, as a monoanionic bidentate ligand, any of a monoanionic bidentate ligand having a β-diketone structure, a monoanionic bidentate ligand having a carboxyl group, a monoanionic bidentate ligand having a phenolic hydroxyl group, and a monoanionic bidentate ligand where two ligand atoms are both nitrogen is preferable because of ease of synthesis.

Note that, among the above substituents, a fluoro group and a trifluoromethyl group each have an advantageous effect of making light-emission wavelength into a short wavelength; therefore, these groups are appropriate particularly in the present invention. It is considered that the cause is that, by introducing such an electron-withdrawing substituent as a fluoro group or a trifluoromethyl group, energy of a HOMO level of an organometallic complex is stabilized. This is because the HOMO level of an organometallic complex is decreased, thereby increasing an energy gap due to the decrease.

In addition, in the organometallic complex represented by the general formula (G6) or (G8), it is preferable that L be a ligand represented by any of the following structural formulas (1) to (5).

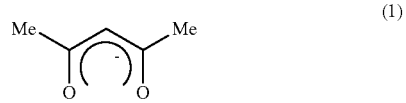

(1)

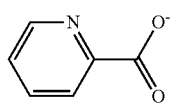

(2)

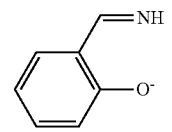

(3)

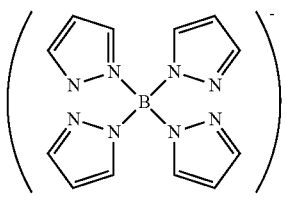

(4)

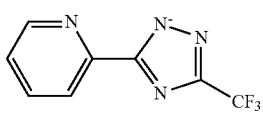

(5)

Another aspect of the present invention is an organometallic complex having a structure represented by a general formula (G9).

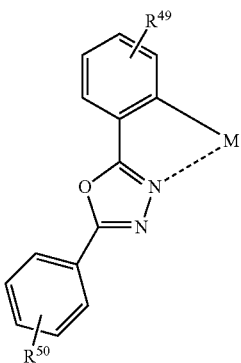

(G9)

In the general formula (G9), $R^{49}$ and $R^{50}$ each represent any of hydrogen, an alkyl group or a cycloalkyl group having 1 to 6 carbon atoms, an alkoxy group having 1 to 6 carbon atoms, an alkoxycarbonyl group having 1 to 6 carbon atoms, an acyl group having 1 to 6 carbon atoms, an acyloxy group having 1 to 6 carbon atoms, a halogen group, a haloalkyl group, and an aryl group having 6 to 12 carbon atoms. In addition, M represents an element belonging to Group 9 or 10. Here, a group of any of a methyl group, an ethyl group, an isopropyl group, and a tert-butyl group is particularly preferable for an alkyl group. In addition, a cyclohexyl group is preferable for a cycloalkyl group. Moreover, a methoxy group is particularly preferable for an alkoxy group. Further, a methoxycarbonyl group is preferable for an alkoxycarbonyl group. An acetyl group is preferable for an acyl group. An acetoxy group is preferable for an acyloxy group. A fluoro group is preferable for a halogen group. A trifluoromethyl group is preferable for a haloalkyl group. Still further, an aryl group may have a substituent, and any of a phenyl group, a phenyl group substituted for a fluoro group, and a phenyl group substituted for a trifluoromethyl group is particularly preferable for an aryl group. Furthermore, iridium is particularly preferable for the element belonging to Group 9, and platinum is particularly preferable for the element belonging to Group 10.

Note that, among the above substituents, a fluoro group and a trifluoromethyl group each have an advantageous effect of making light-emission wavelength into a short wavelength; therefore, these groups are appropriate particularly in the present invention. It is considered that the cause is that, by introducing such an electron-withdrawing substituent as a fluoro group or a trifluoromethyl group, energy of a HOMO level of an organometallic complex is stabilized. This is because the HOMO level of an organometallic complex is decreased, thereby increasing an energy gap due to the decrease.

Another aspect of the present invention is an organometallic complex represented by a general formula (G10).

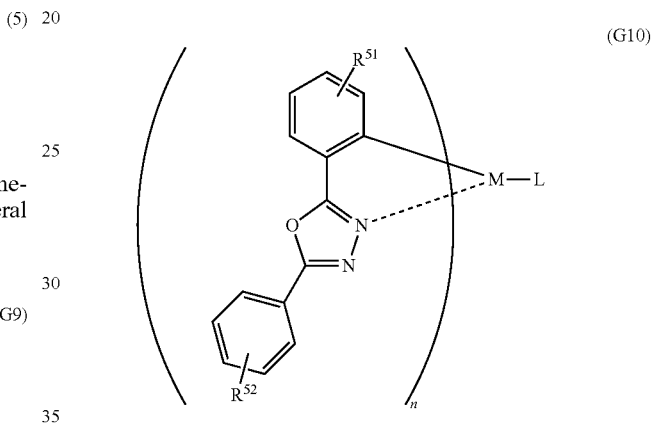

(G10)

In the general formula (G10), $R^{51}$ and $R^{52}$ each represent any of hydrogen, an alkyl group or a cycloalkyl group having 1 to 6 carbon atoms, an alkoxy group having 1 to 6 carbon atoms, an alkoxycarbonyl group having 1 to 6 carbon atoms, an acyl group having 1 to 6 carbon atoms, an acyloxy group having 1 to 6 carbon atoms, a halogen group, a haloalkyl group, and an aryl group having 6 to 12 carbon atoms. In addition, M represents an element belonging to Group 9 or 10. When M is an element belonging to Group 9, n=2, whereas, when M is an element belonging to Group 10, n=1. L represents a monoanionic bidentate ligand. Here, a group of any of a methyl group, an ethyl group, an isopropyl group, and a ten-butyl group is particularly preferable for an alkyl group. In addition, a cyclohexyl group is preferable for a cycloalkyl group. Moreover, a methoxy group is particularly preferable for an alkoxy group. Further, a methoxycarbonyl group is preferable for an alkoxycarbonyl group. An acetyl group is preferable for an acyl group. An acetoxy group is preferable for an acyloxy group. A fluoro group is preferable for a halogen group. A trifluoromethyl group is preferable for a haloalkyl group. Still further, an aryl group may have a substituent, and any of a phenyl group, a phenyl group substituted for a fluoro group, and a phenyl group substituted for a trifluoromethyl group is particularly preferable for an aryl group. Furthermore, iridium is particularly preferable for the element belonging to Group 9, and platinum is particularly preferable for the element belonging to Group 10. In addition, as a monoanionic bidentate ligand, any of a monoanionic bidentate ligand having a β-diketone structure, a monoanionic bidentate ligand having a carboxyl group, a monoanionic bidentate ligand having a phenolic hydroxyl group, and a monoanionic bidentate ligand where two ligand atoms are both nitrogen is preferable because of ease of synthesis.

Note that, among the above substituents, a fluoro group and a trifluoromethyl group each have an advantageous effect of making light-emission wavelength into a short wavelength; therefore, these groups are appropriate particularly in the present invention. It is considered that the cause is that, by introducing such an electron-withdrawing substituent as a fluoro group or a trifluoromethyl group, energy of a HOMO level of an organometallic complex is stabilized. This is because the HOMO level of an organometallic complex is decreased, thereby increasing an energy gap due to the decrease.

Another aspect of the present invention is an organometallic complex having a structure represented by a general formula (G11). Note that, as in the general formula (G11), from the perspective of luminous efficiency and heat resistance, iridium is preferable to platinum as the central metal.

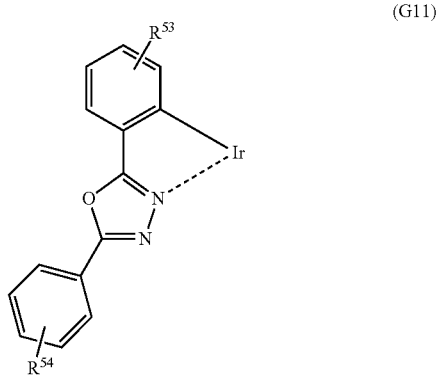

(G11)

In the general formula (G11), $R^{53}$ and $R^{54}$ each represent any of hydrogen, an alkyl group or a cycloalkyl group having 1 to 6 carbon atoms, an alkoxy group having 1 to 6 carbon atoms, an alkoxycarbonyl group having 1 to 6 carbon atoms, an acyl group having 1 to 6 carbon atoms, an acyloxy group having 1 to 6 carbon atoms, a halogen group, a haloalkyl group, and an aryl group having 6 to 12 carbon atoms. Here, a group of any of a methyl group, an ethyl group, an isopropyl group, and a tert-butyl group is particularly preferable for an alkyl group. In addition, a cyclohexyl group is preferable for a cycloalkyl group. Moreover, a methoxy group is particularly preferable for an alkoxy group. Further, a methoxycarbonyl group is preferable for an alkoxycarbonyl group. An acetyl group is preferable for an acyl group. An acetoxy group is preferable for an acyloxy group. A fluoro group is preferable for a halogen group. A trifluoromethyl group is preferable for a haloalkyl group. Still further, an aryl group may have a substituent, and any of a phenyl group, a phenyl group substituted for a fluoro group, and a phenyl group substituted for a trifluoromethyl group is particularly preferable for an aryl group.

Note that, among the above substituents, a fluoro group and a trifluoromethyl group each have an advantageous effect of making light-emission wavelength into a short wavelength; therefore, these groups are appropriate particularly in the present invention. It is considered that the cause is that, by introducing such an electron-withdrawing substituent as a fluoro group or a trifluoromethyl group, energy of a HOMO level of an organometallic complex is stabilized. This is because the HOMO level of an organometallic complex is decreased, thereby increasing an energy gap due to the decrease.

Another aspect of the present invention is an organometallic complex represented by a general formula (O12). Note that, as in the general formula (G12), from the perspective of luminous efficiency and heat resistance, iridium is preferable to platinum as the central metal.

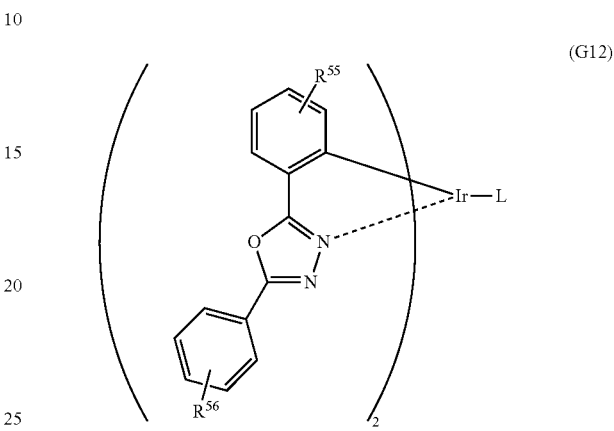

(G12)

In the general formula (G12), $R^{55}$ and $R^{56}$ each represent any of hydrogen, an alkyl group or a cycloalkyl group having 1 to 6 carbon atoms, an alkoxy group having 1 to 6 carbon atoms, an alkoxycarbonyl group having 1 to 6 carbon atoms, an acyl group having 1 to 6 carbon atoms, an acyloxy group having 1 to 6 carbon atoms, a halogen group, a haloalkyl group, and an aryl group having 6 to 12 carbon atoms. In addition, L represents a monoanionic bidentate ligand. Here, a group of any of a methyl group, an ethyl group, an isopropyl group, and a tert-butyl group is particularly preferable for an alkyl group. In addition, a cyclohexyl group is preferable for a cycloalkyl group. Moreover, a methoxy group is particularly preferable for an alkoxy group. Further, a methoxycarbonyl group is preferable for an alkoxycarbonyl group. An acetyl group is preferable for an acyl group. An acetoxy group is preferable for an acyloxy group. A fluoro group is preferable for a halogen group. A trifluoromethyl group is preferable for a haloalkyl group. Still further, an aryl group may have a substituent, and any of a phenyl group, a phenyl group substituted for a fluoro group, and a phenyl group substituted for a trifluoromethyl group is particularly preferable for an aryl group. In addition, as a monoanionic bidentate ligand, any of a monoanionic bidentate ligand having a β-diketone structure, a monoanionic bidentate ligand having a carboxyl group, a monoanionic bidentate ligand having a phenolic hydroxyl group, and a monoanionic bidentate ligand where two ligand atoms are both nitrogen is preferable because of ease of synthesis.

Note that, among the above substituents, a fluoro group and a trifluoromethyl group each have an advantageous effect of making light-emission wavelength into a short wavelength; therefore, these groups are appropriate particularly in the present invention. It is considered that the cause is that, by introducing such an electron-withdrawing substituent as a fluoro group or a trifluoromethyl group, energy of a HOMO level of an organometallic complex is stabilized. This is because the HOMO level of an organometallic complex is decreased, thereby increasing an energy gap due to the decrease.

In addition, in the organometallic complex represented by the general formula (G10) or (G12), it is preferable that L be a ligand represented by any of the following structural formulas (1) to (5).

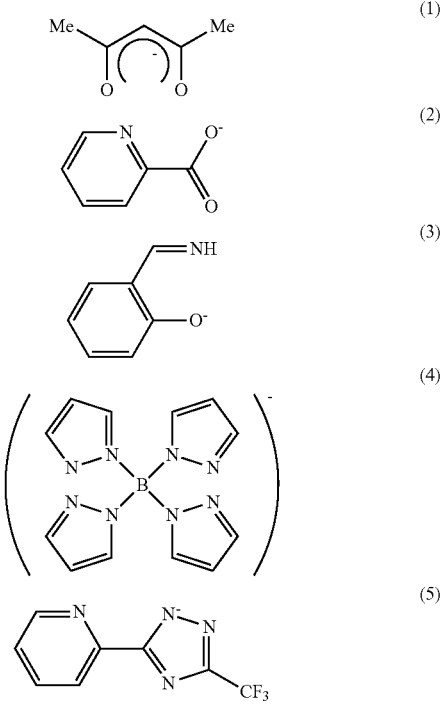

Another aspect of the present invention is a light-emitting element containing an organometallic complex having a structure represented by any of the above general formulas (G1), (G3), (G5), (G7), (G9), and (G11), or an organometallic complex represented by any of the general formulas (G2), (G4), (G6), (G8), (G10), and (G12).

It is preferable that the light-emitting element have a structure where a layer containing the organometallic complex having a structure represented by any of the general formulas (G1), (G3), (G5), (G7), (G9), and (G11), or the organometallic complex represented by any of the general formulas (G2), (G4), (G6), (G8), (G10), and (G12) is provided between electrodes, and the organometallic complex emits light when current flows between electrodes. In such a manner, since the light-emitting element using the organometallic complex of the present invention as a light-emitting substance can obtain phosphorescence, light is emitted efficiently.

In addition, light emission having a wavelength band of green to blue can be obtained. Therefore, another aspect of the present invention is a light-emitting element where the organometallic complex having a structure represented by any of the general formulas (G1), (G3), (G5), (G7), (G9), and (G11), or the organometallic complex represented by any of the general formulas (G2), (G4), (G6), (G8), (G10), and (G12) is used as a light-emitting substance.

Note that the organometallic complex of the present invention can be used in combination with a fluorescent material and can also be used for usage of increasing luminous efficiency of the fluorescent material. In other words, in the light-emitting element, the organometallic complex can also be used as a sensitizer for the fluorescent material.

In addition, another aspect of the present invention is a light-emitting device where a plurality of the above light-emitting elements is disposed.

Moreover, another aspect of the present invention is a light-emitting device where the above light-emitting device is used as a pixel or a light source.

Further, another aspect of the present invention is an electronic device where the above light-emitting element is used for a display portion.

According to the present invention, an organometallic complex which can emit phosphoresce can be obtained. In particular, an organometallic complex emitting phosphorescence having a wavelength band of green to blue can be obtained. In addition, an organometallic complex that emits phosphorescence and that is superior in heat resistance can be obtained. Moreover, according to the present invention, an organometallic complex that can be used as a sensitizer can be obtained.

By using an organometallic complex of the present invention as a light-emitting substance, a high-efficient light-emitting element that can emit green, bluish green, or blue-based light can be obtained. In addition, by using an organometallic complex of the present invention as a sensitizer, a light-emitting element that can emit light efficiently can be obtained.

BRIEF DESCRIPTION OF DRAWINGS

In the accompanying drawings:

FIG. 5 is a diagram explaining a frame operation of a light-emitting device to which the present invention is applied;

DETAILED DESCRIPTION OF THE INVENTION

Embodiment modes of the present invention will be explained hereinafter with reference to the accompanying drawings. However, it is to be easily understood that various changes and modifications will be apparent to those skilled in the art. Therefore, unless such changes and modifications depart from the purport and the scope of the present invention, they should be construed as being included therein.

Note that, according to the present invention, among a pair of electrodes of a light-emitting element, an electrode that serves as an anode refers to an electrode that can obtain light emission in applying a higher voltage to this electrode, and an electrode that serves as a cathode refers to an electrode that can obtain light emission in applying a lower voltage to this electrode.

Embodiment Mode 1

This embodiment mode will explain an organometallic complex of the present invention.

Organometallic complexes represented by structural formulas (6) to (84) can be given as one mode of the present invention. However, the present invention is not limited to the description here.

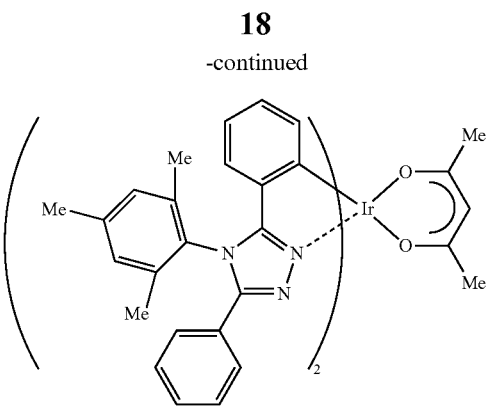

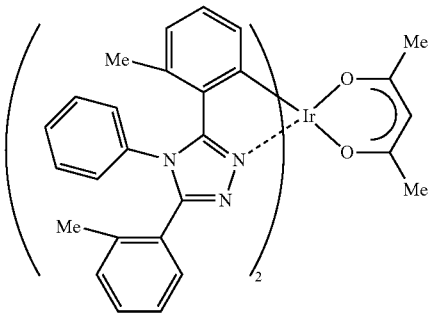

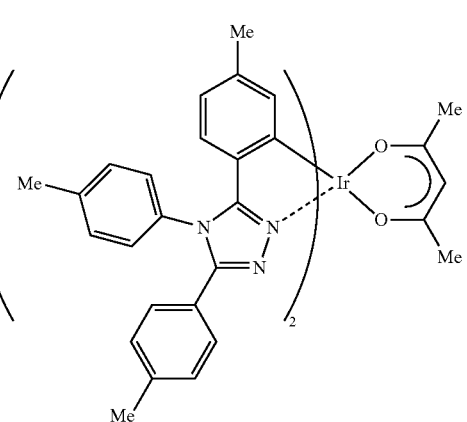

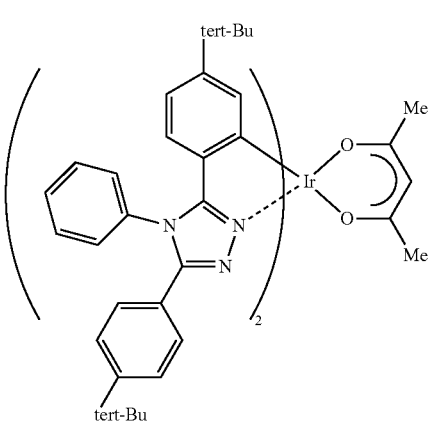

(13)
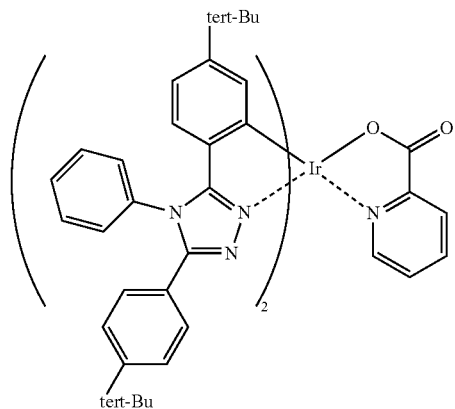
(14)
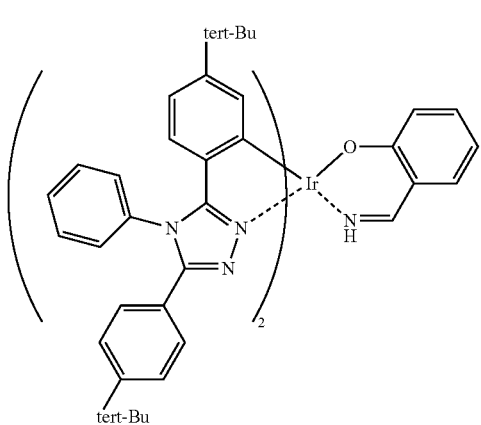
(15)
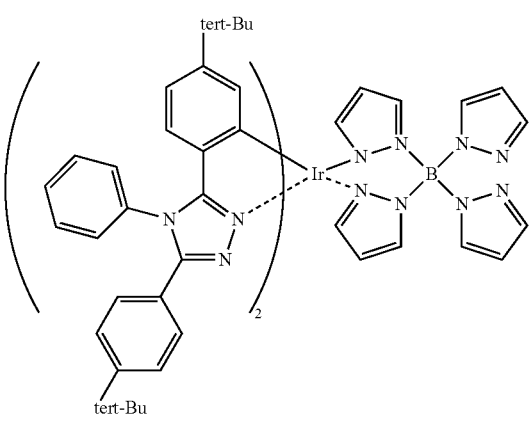
(16)
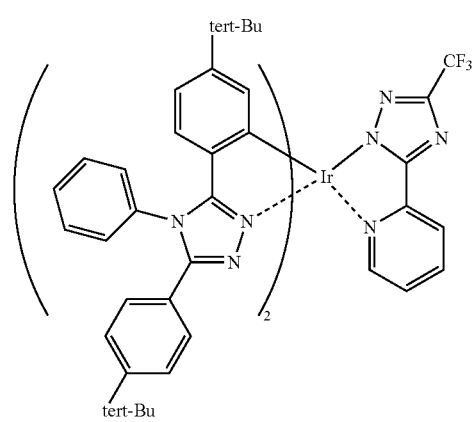
(17)
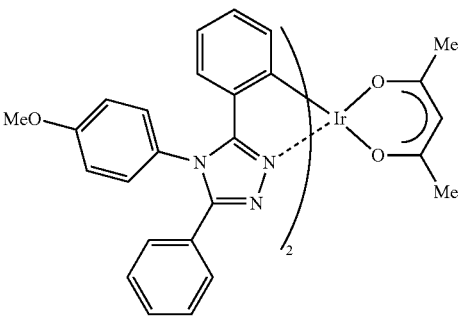
(18)
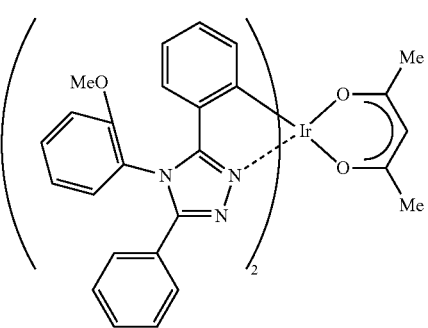
(19)
(20)
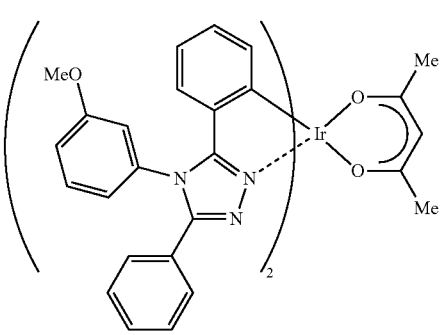

-continued
(21)
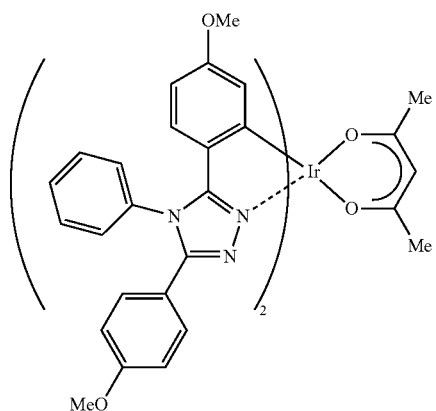
(22)
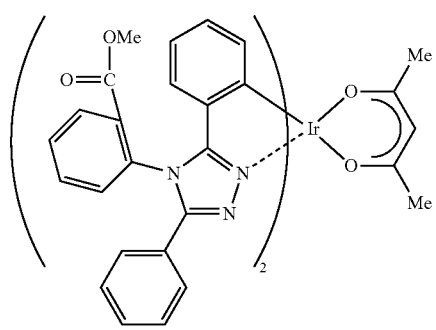
(23)
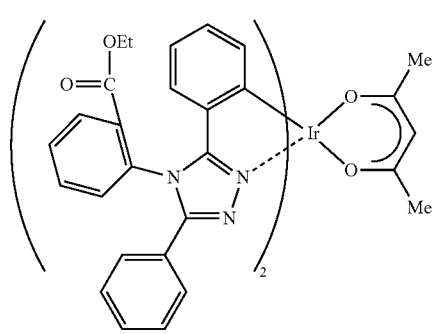
(24)
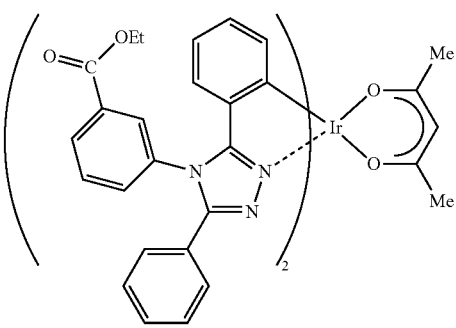
(25)
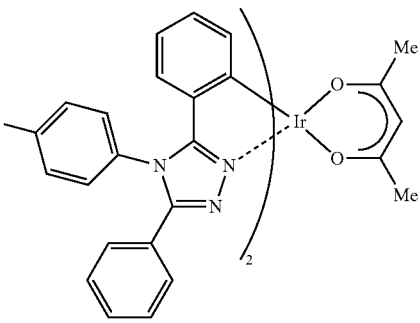
(26)
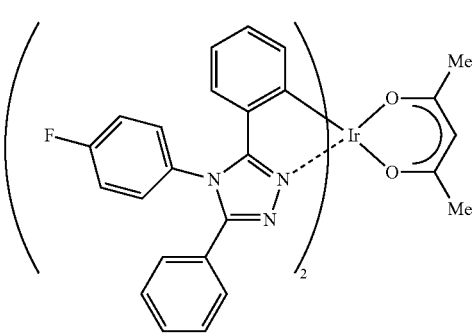
(27)
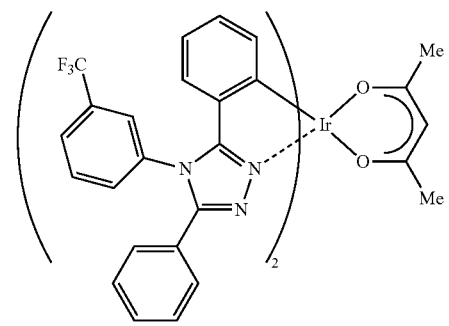
(28)
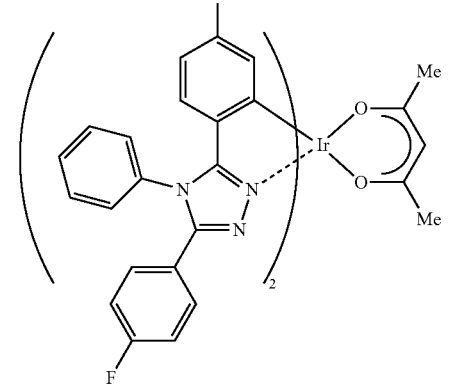

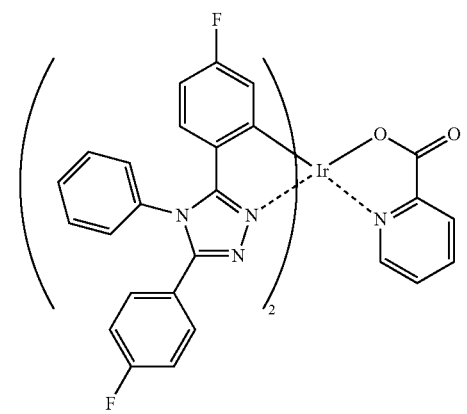
(29)
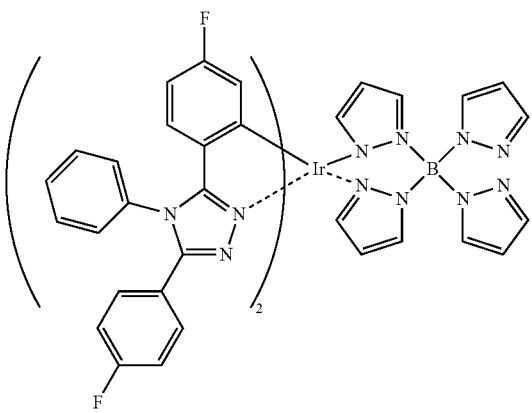
(30)
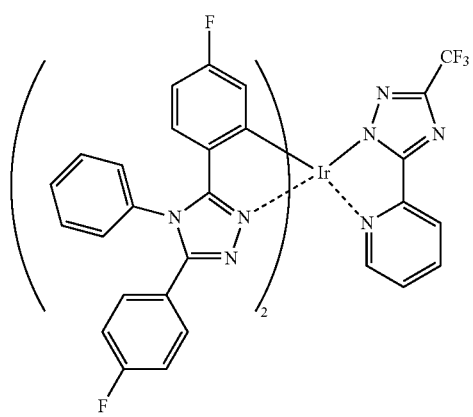
(31)
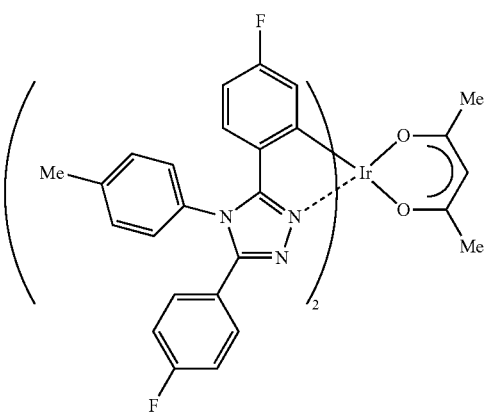
(32)
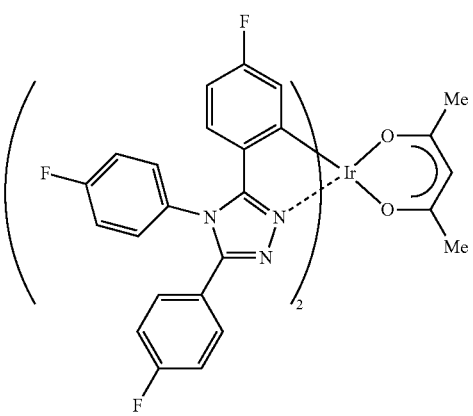
(33)
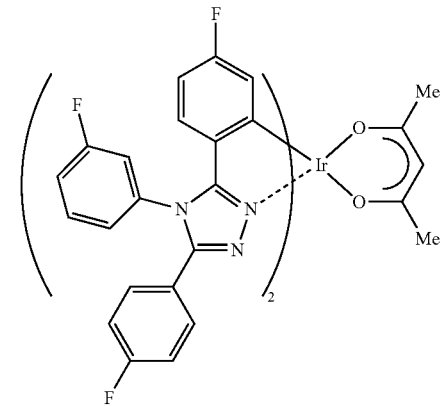
(34)
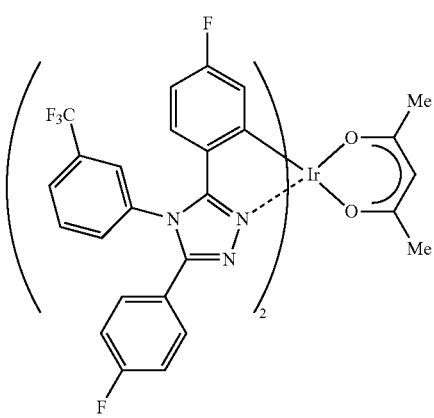
(35)
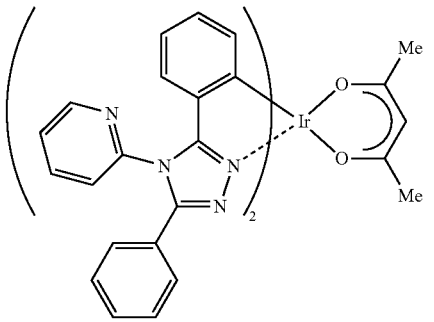
(36)

(37) 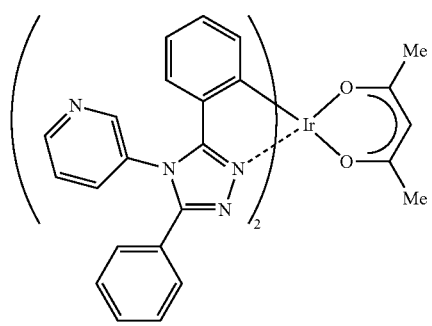
(38) 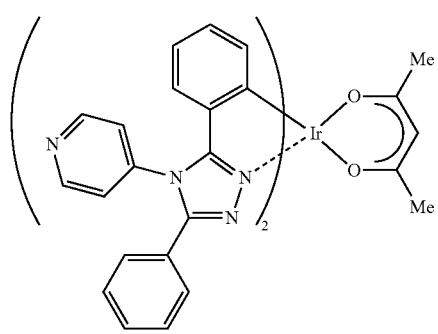
(39) 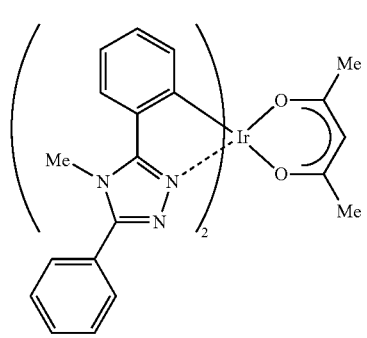
(40) 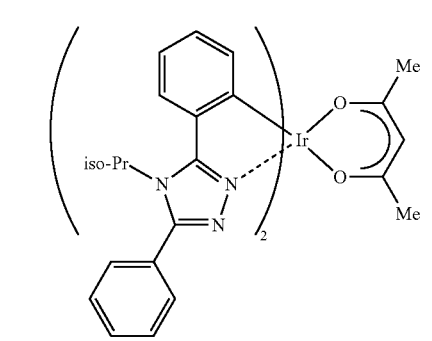
(41) 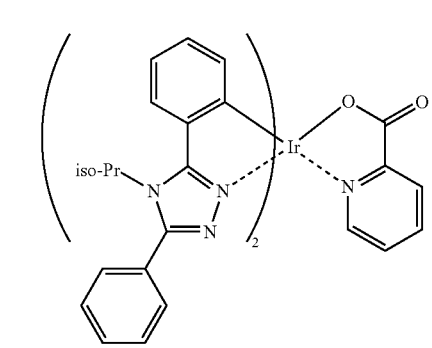
(42) 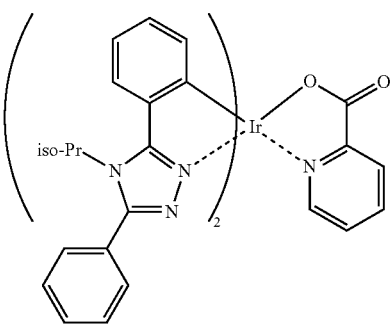
(43) 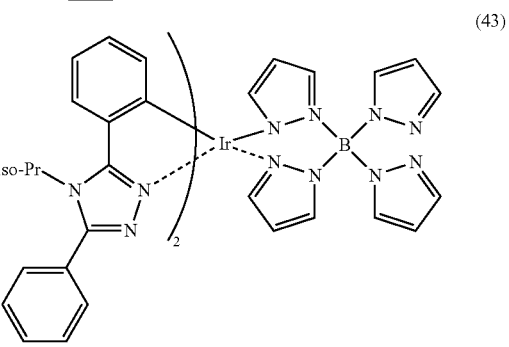
(44) 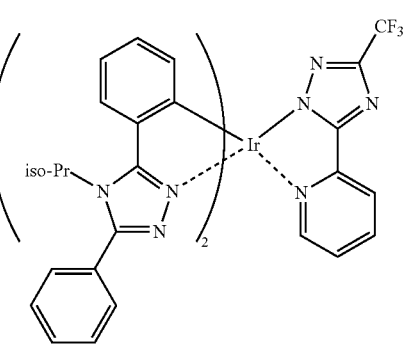
(45) 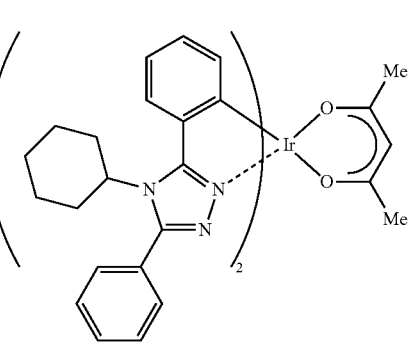
(46) 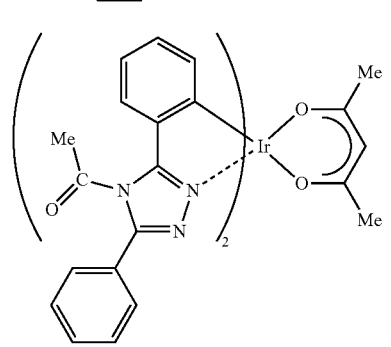

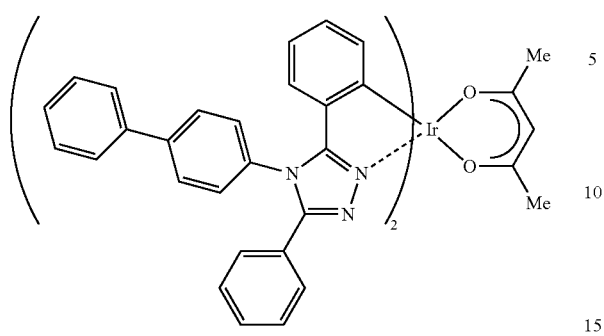
(47)
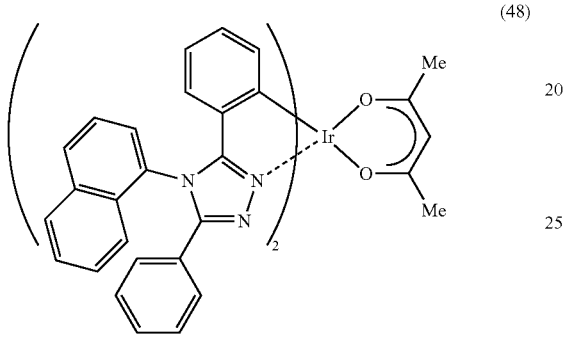
(48)
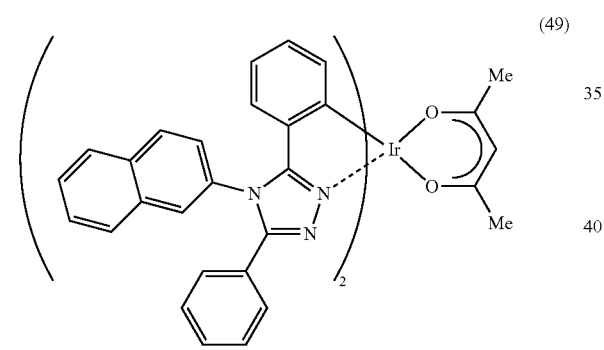
(49)
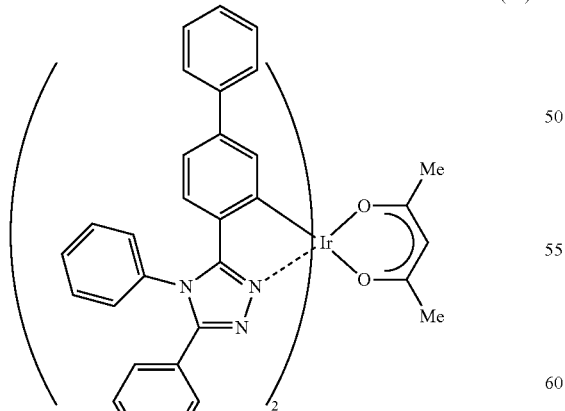
(50)
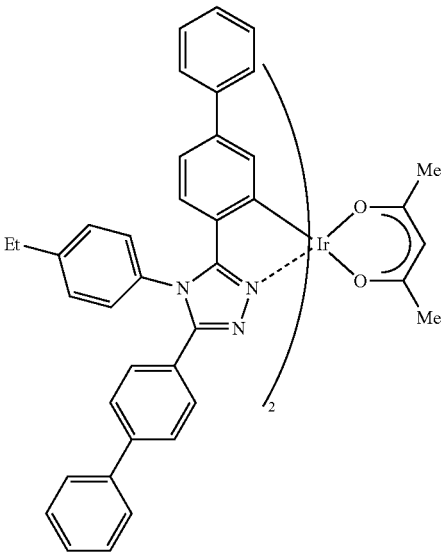
(51)
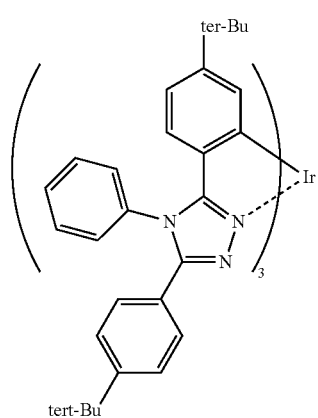
(52)
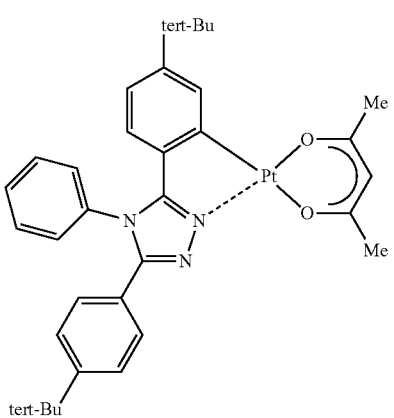
(53)

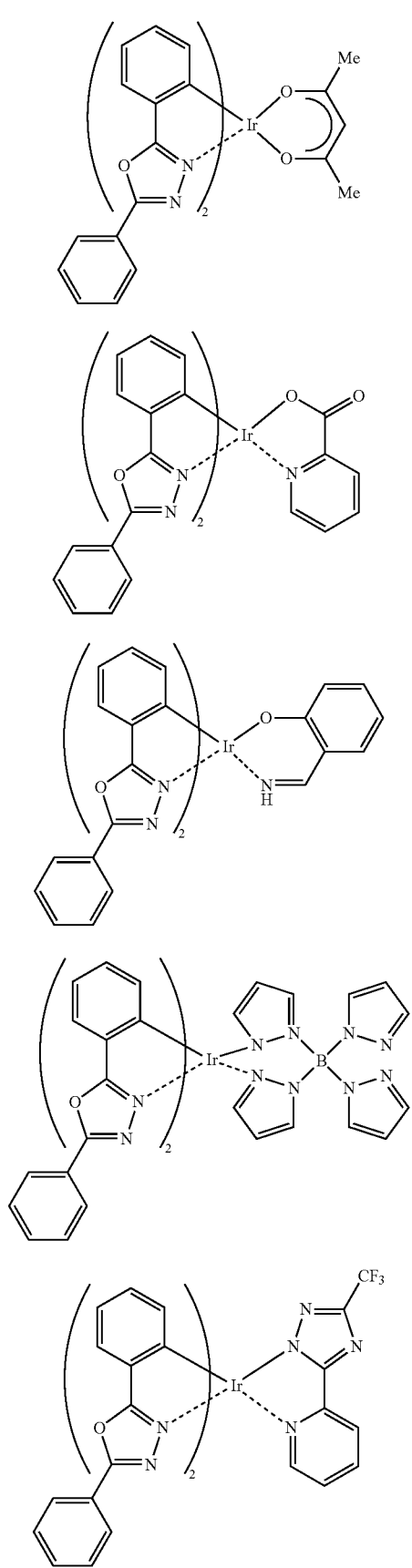
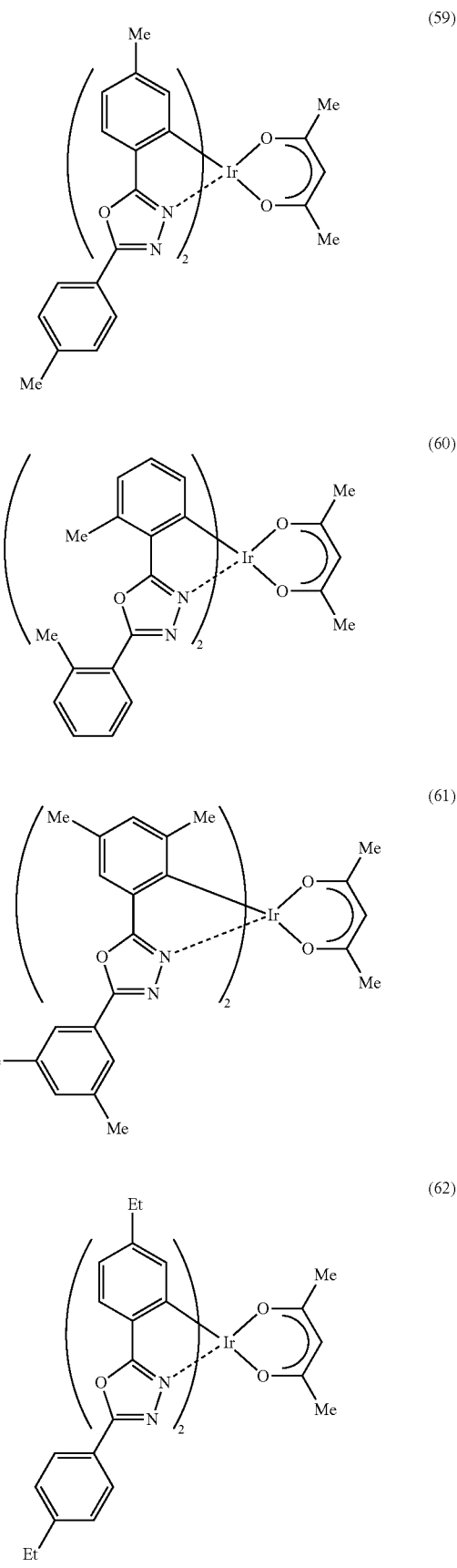

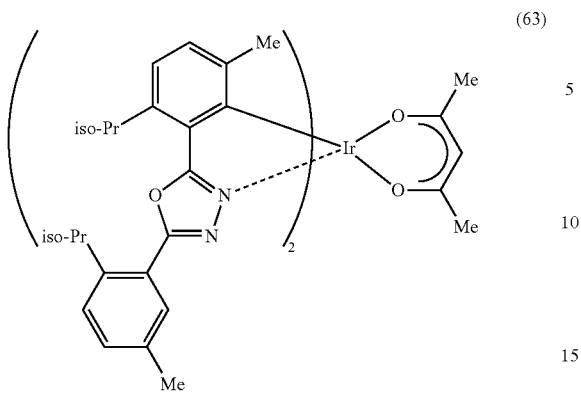
(63)
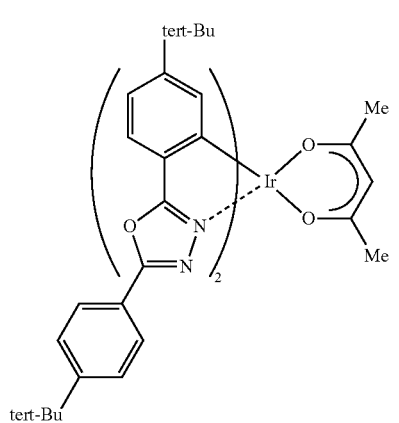
(64)
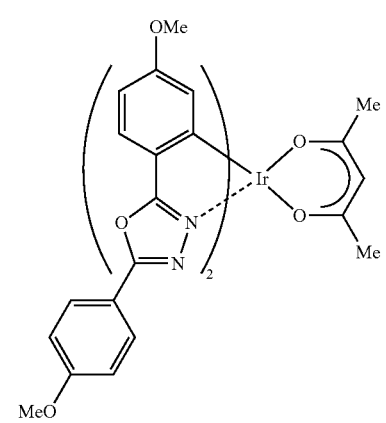
(65)
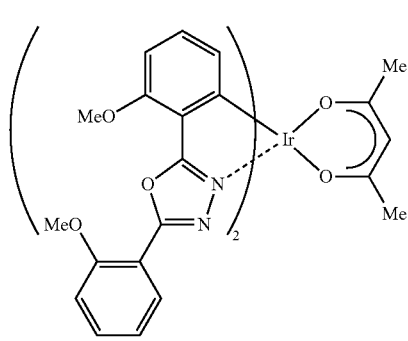
(66)
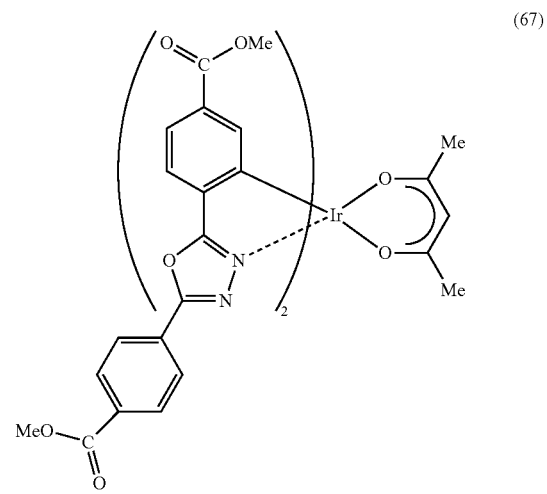
(67)
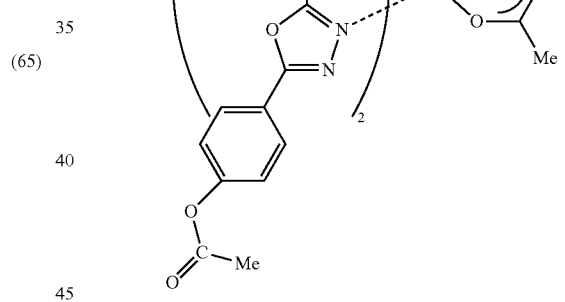
(68)
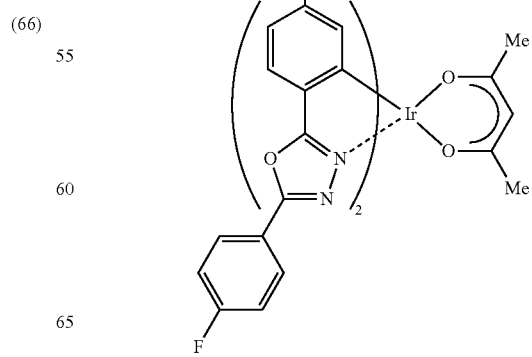
(69)

33
-continued
(70)
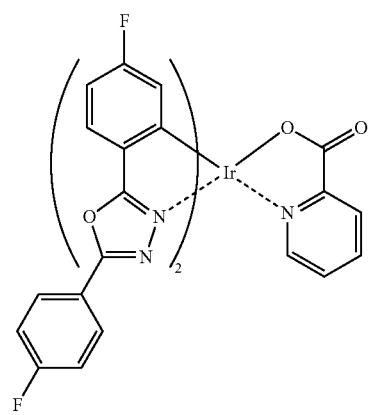
(71)
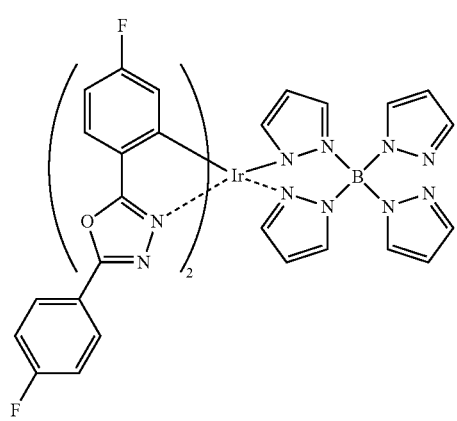
(72)
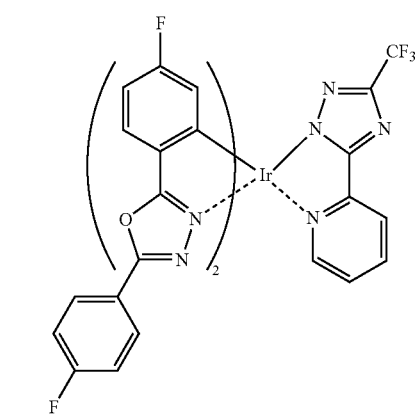
(73)
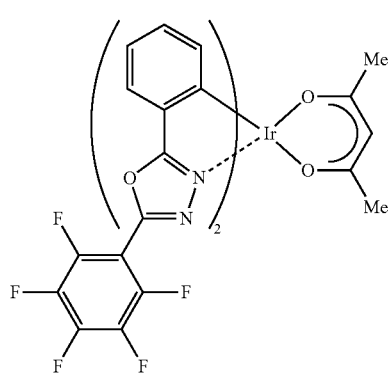
34
-continued
(74)
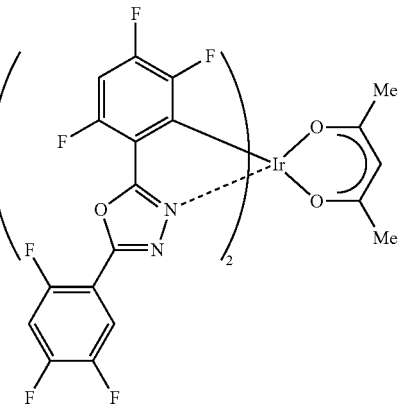
(75)
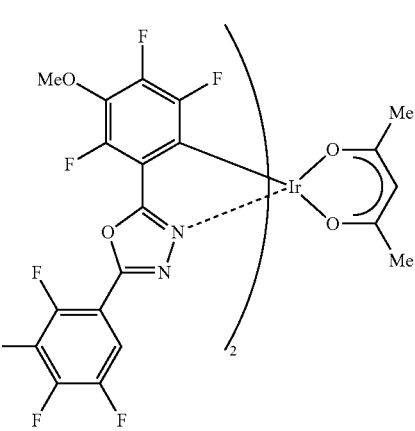
(76)
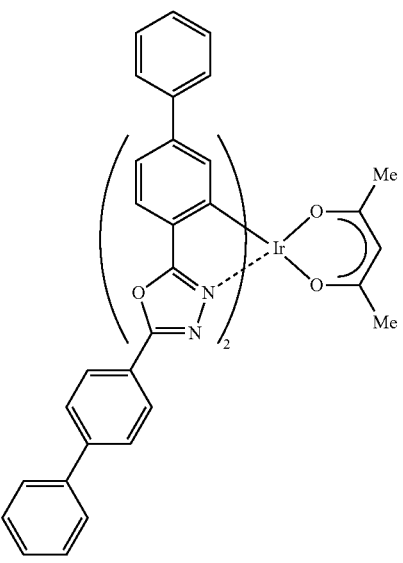

(77)
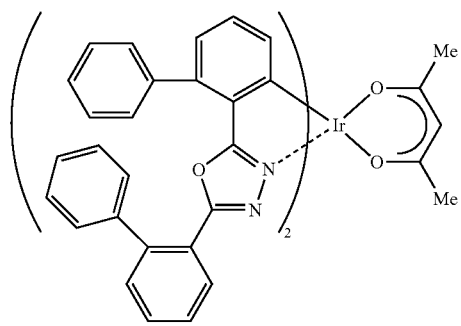
(78)
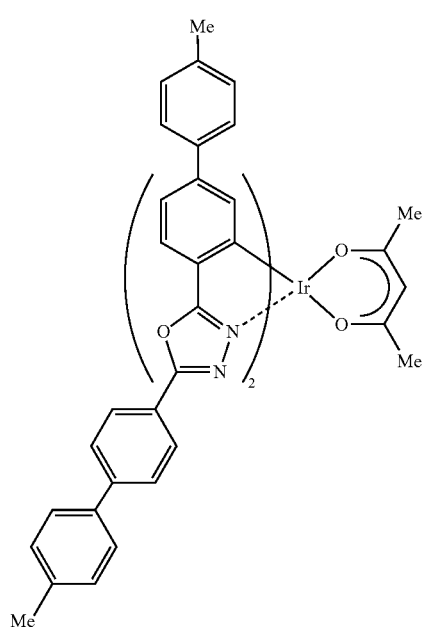
(79)
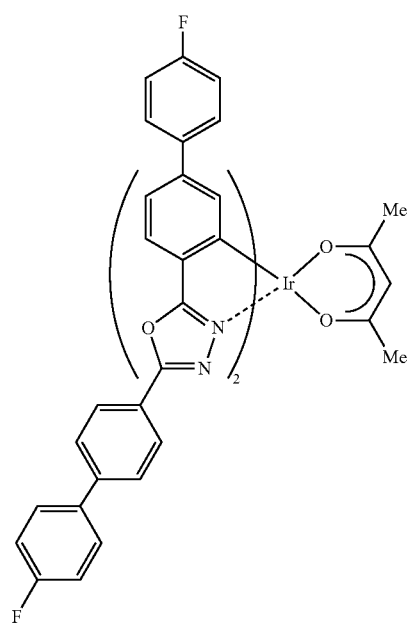
(80)
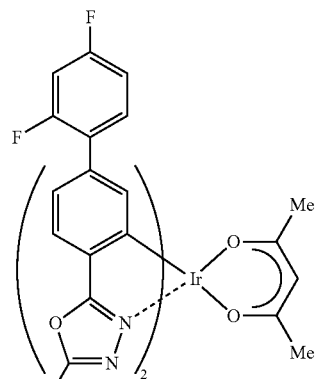
(81)
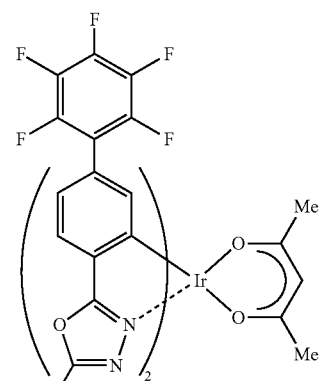
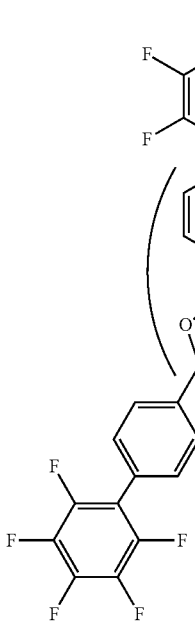

(82)

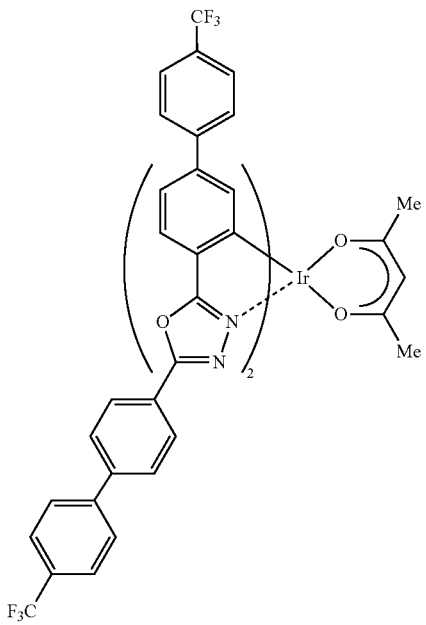

(83)

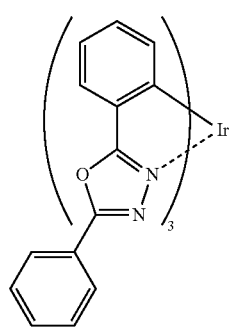

(84)

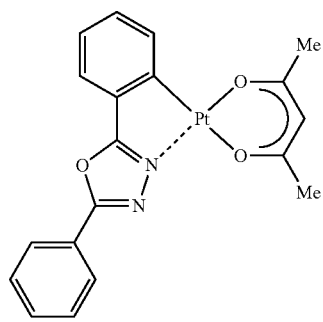

Each of the organometallic complexes of the present invention described above emits phosphorescence. Therefore, by using an organometallic complex of the present invention as a light-emitting substance, a light-emitting element having high internal quantum efficiency and luminous efficiency can be manufactured.

In addition, an organometallic complex generally has poor heat resistance. However, an organometallic complex of the present invention emits phosphoresce and is superior in heat resistance.

Embodiment Mode 2

A mode of a light-emitting element in which an organometallic complex of the present invention is used as a light-emitting substance will be explained with reference to FIG. 1.

Figure 1:
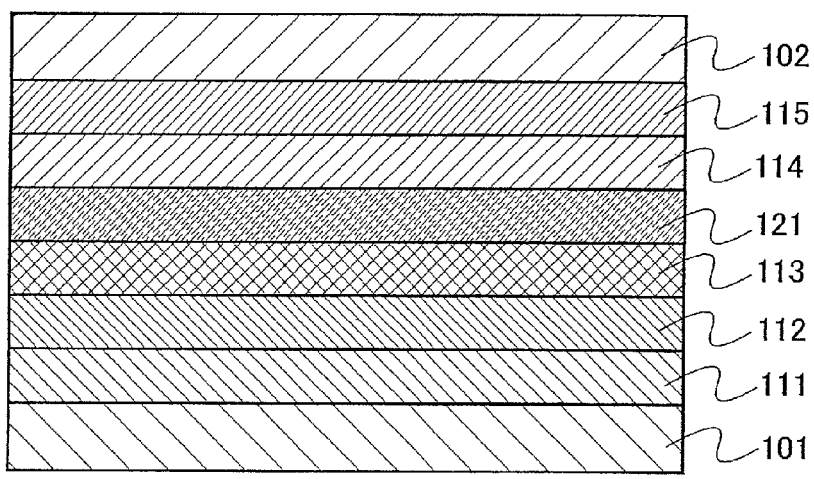
FIG. 1 is a view explaining one mode of a light-emitting device according to the present invention.

FIG. 1 shows a light-emitting element having a light-emitting between a first electrode 101 and a second electrode 102. Then, the light-emitting layer 113 contains an organometallic complex according to the present invention having a structure represented by any of general formulas (G1), (G3), (G5), (G7), (G9), and (G11), or an organometallic complex according to the present invention represented by any of general formulas (G2), (G4), (G6), (G8), (G10), and (G12).

In addition to the light-emitting layer 113, a hole-injecting layer 111, a hole-transporting layer 112, an electron-transporting layer 114, an electron-injecting layer 115, a hole-blocking layer 121, or the like is provided between the first electrode 101 and the second electrode 102. These layers are stacked so that holes are injected from the first electrode 101 side and electrons are injected from the second electrode 102 side when a voltage is applied so that the potential of the first electrode 101 gets higher than that of the second electrode 102.

Here, the hole-blocking layer is a layer having a function of preventing the holes injected from the first electrode 101 side from penetrating the light-emitting layer 113 to the other electrode side, and a function of preventing excitation energy generated in the light-emitting layer from moving to other layer from the light-emitting layer, as well as transporting the holes to the light-emitting layer. As shown in FIG. 1, the hole-blocking layer is provided between the light-emitting layer 113 and the electron-transporting layer 114, which can prevent the holes from penetrating.

In such a light-emitting element, the holes injected from the first electrode 101 side and the electrons injected from the second electrode 102 side are recombined in the light-emitting layer 113, and the organometallic complex is made into an excitation state. An organometallic complex in an excited state emits light upon returning to a ground state. Thus, an organometallic complex according to the present invention serves as a light-emitting substance.

By using an organometallic complex according to the present invention as a light-emitting substance, a light-emitting element having high internal quantum efficiency and luminous efficiency can be manufactured. Further, since an organometallic complex according to the present invention is superior in heat resistance, a light-emitting element using such an organometallic complex as a light-emitting substance is superior in heat stability. Consequently, a high-reliable light-emitting element can be obtained.

Here, the light-emitting layer 113 is a layer containing an organometallic complex according to the present invention. The light-emitting layer 113 may be a layer formed only of an organometallic complex according to the present invention. However, when concentration quenching occurs, it is preferable to form a layer in which an organometallic complex (a guest) is mixed to be dispersed in a layer (a host) formed of a substance having an energy gap larger than that of an organometallic complex. By containing an organometallic complex according to the present invention in the light-emitting layer 113 by being dispersed, light emission can be prevented from being quenched due to the concentration. Here, the energy gap refers to an energy gap between the LUMO level and the HOMO level. By using an organometallic complex according to the present invention for the light-emitting layer 113, a high-efficient light-emitting element whose wavelength band is green to blue light can be obtained.

The substance to be used for dispersing an organometallic complex according to the present invention is not particularly limited, and a carbazole derivative such as 4,4'-bis(N-carbazolyl)biphenyl (abbreviation: CBP) or 4,4',4"-tris(N-carbazolyl)triphenylamine (abbreviation: TCTA); a metal complex such as bis[2-(2-hydroxyphenyl)pyridinato]zinc (abbreviation: $Znpp_2$), bis[2-(2-hydroxyphenyl)benzoxazolate]zinc (abbreviation: ZnBOX); or the like is preferable in addition to an arylamine derivative such as 1,1-bis[4-(N,N-diphenylamino)phenyl]cyclohexane (TPAC). One or more of these substances are preferably selected to be mixed so that an organometallic complex according to the present invention is dispersed. A layer where a plurality of compounds is thus mixed can be formed with the use of a co-evaporation method. Here, co-evaporation refers to an evaporation method in which raw materials are respectively vaporized from a plurality of evaporation sources provided in one treatment chamber, and the vaporized materials are mixed in a gas-phase state to be deposited over a subject.

Note that the light-emitting layer 113 can be formed by a droplet-discharging method instead of an evaporation method. By using a droplet-discharging method, a raw material of a predetermined amount can be discharged at a predetermined place; therefore, the cost of a raw material can be reduced.

In addition, the first electrode 101 and the second electrode 102 are not particularly limited and can be formed using gold (Au), platinum (Pt), nickel (Ni), tungsten (W), chromium (Cr), molybdenum (Mo), iron (Fe), cobalt (Co), copper (Cu), palladium (Pd), or the like as well as indium tin oxide (ITO), indium tin oxide containing silicon oxide, or indium oxide formed by using a target mixed with 2 wt. % to 20 wt. % of zinc oxide. Moreover, in addition to aluminum, an alloy of magnesium and silver, an alloy of aluminum and lithium, or the like can also be used in forming the first electrode 101. Note that a method for forming the first electrode 101 and the second electrode 102 is not particularly limited and, for example, a sputtering method, an evaporation method, or the like can be used. Note that it is preferable to form either the first electrode 101 or the second electrode 102, or both by using indium tin oxide or the like or by depositing silver, aluminum, or the like to have a thickness of several nm to several 10 nm so that emitted light can be extracted to outside.

Moreover, the hole-transporting layer 112 may be provided between the first electrode 101 and the light-emitting layer 113 as shown in FIG. 1. Here, the hole-transporting layer 112 is a layer having a function of transporting the holes injected from the first electrode 101 side to the light-emitting layer 113. By providing the hole-transporting layer 112 in such a manner, the distance between the first electrode 101 and the light-emitting layer 113 can be larger. Consequently, light emission can be prevented from being quenched due to metal contained in the first electrode 101. The hole-transporting layer 112 is preferable to be formed using a substance having high hole transportability and particularly preferable to be formed using a substance having hole mobility of $1\times10^{-6}$ $cm^2/Vs$ or more. Note that the substance having high hole transportability indicates a substance having higher mobility of holes than that of electrons, where a value of a ratio of hole mobility to electron mobility (=hole mobility/electron mobility) is more than 100.

The following can be given as a specific example of a substance that can be used to form the hole-transporting layer 112: 4,4'-bis[N-(1-naphthyl)-N-phenylamino]biphenyl (abbreviation: NPB); 4,4'-bis[N-(3-methylphenyl)-N-phenylamino]biphenyl (abbreviation: TPD); 4,4',4"-tris(N,N-diphenylamino)triphenylamine (abbreviation: TDATA); -tris[N-(3-methylphenyl)-N-phenylamino]triphenylamine (abbreviation: MTDATA); 4,4'-bis{N-[4-(N,N-di-m-tolylamino)phenyl]-N-phenylamino}biphenyl (abbreviation: DNTPD); 1,3,5-tris[N,N-di(m-tolyl)amino]benzene (abbreviation: m-MTDAB); 4,4',4"-tris(N-carbazolyl)triphenylamine (abbreviation: TCTA); phthalocyanine (abbreviation: $H_2Pc$); copper phthalocyanine (abbreviation: CuPc); vanadylphthalocyanine (abbreviation: VOPc); and the like. In addition, the hole-transporting layer 112 may also be a multilayer where two or more layers formed of the above substances are combined.

Further, the electron-transporting layer 114 may be provided between the second electrode 102 and the light-emitting layer 113 as shown in FIG. 1. Here, the electron-transporting layer 114 is a layer having a function of transporting the electrons injected from the second electrode 102 side to the light-emitting layer 113. By providing the electron-transporting layer 114 in such a manner, the distance between the second electrode 102 and the light-emitting layer 113 can be larger. Consequently, light emission can be prevented from being quenched due to metal contained in the second electrode 102. The electron-transporting layer 114 is preferable to be formed using a substance having high electron transportability and particularly preferable to be formed using a substance having electron mobility of $1\times10^{-6}$ $cm^2Ns$ or more. Note that the substance having high electron transportability refers to a substance having higher mobility of electrons than that of holes, where, preferably, a value of a ratio of electron mobility to hole mobility (=electron mobility/hole mobility) is more than 100.

The following can be given as a specific example of a substance that can be used to form the electron-transporting layer 114: 2-(4-biphenylyl)-5-(4-tert-butylphenyl)-1,3,4-oxadiazole (abbreviation: PBD); 1,3-bis[5-(p-tert-butylphenyl)-1,3,4-oxadiazole-2-yl]benzene (abbreviation: OXD-7); 3-(4-tert-butylphenyl))-4-phenyl-5-(4-biphenylyl)-1,2,4-triazole (abbreviation: TAZ); 3-(4-tert butylphenyl)-4-(4-ethylphenyl)-5-(4-biphenylyl)-1,2,4-triazole (abbreviation: p-EtTAZ); bathophenanthroline (abbreviation: BPhen); bathocuproin (abbreviation: BCP); 4,4-bis(5-methylbenzoxazol-2-yl)stilbene (abbreviation: BzOs); and the like as well as a metal complex such as tris(8-quinolinolato)aluminum (abbreviation: $Alq_3$); tris(4-methyl-8-quinolinolato)aluminum (abbreviation: $Almq_3$); bis(10-hydroxybenzo[h]-quinolinato)berylium (abbreviation: $BeBq_2$); bis(2-methyl-8-quinolinolato)-4-phenylphenolate-aluminum (abbreviation: BAlq); bis[2-(2-hydroxyphenyl)benzoxazolate]zinc (abbreviation: $Zn(BOX)_2$); and bis[2-(2-hydroxyphenyl) benzothiazolato]zinc (abbreviation: $Zn(BTZ)_2$) In addition, the electron-transporting layer 114 may also be a multilayer where two or more layers formed of the above substances are combined.

Note that the hole-transporting layer 112 and the electron-transporting layer 114 may be each formed by using a bipolar substance in addition to the above substances. The bipolar substance refers to the following substance: when mobility of either carrier of an electron or a hole is compared with mobility of the other carrier, a value of a ratio of one carrier mobility to the other carrier mobility is 100 or less, preferably 10 or less. As for the bipolar substance, for example, 2,3-bis(4-diphenylaminophenyl)quinoxaline (abbreviation: TPAQn); 2,3-bis{4-[N-(1-naphthyl)-N-phenylamino]phenyl}-dibenzo[f,h]quinoxaline (abbreviation: NPADiBzQn); and the like can be given. It is preferable to particularly use a substance of which hole and electron mobility are each $1\times10^{-6}$ cm$^2$/Vs or more in the bipolar substance. In addition, the hole-transporting layer 112 and the electron-transporting layer 114 may be formed by using the same bipolar substance.

Furthermore, the hole-injecting layer 111 may be provided between the first electrode 101 and the hole-transporting layer 112 as shown in FIG. 1. The hole-injecting layer 111 is a layer having a function of assisting holes to be injected to the hole-transporting layer 112 from the first electrode 101. By providing the hole-injecting layer 111, ionization potential difference between the first electrode 101 and the hole-transporting layer 112 is relieved; thus, holes are easily injected. The hole-injecting layer 111 is preferably formed using a substance of which ionization potential is lower than that of a substance forming the hole-transporting layer 112 and higher than that of a substance forming the first electrode 101 or using a substance of which energy band curves by being provided as a thin film of 1 nm to 2 nm between the hole-transporting layer 112 and the first electrode 101.

In other words, the hole-injecting layer 111 can be formed by selecting such a substance of which ionization potential is relatively lower than that of the hole-transporting layer 112. As for a specific example of a substance that can be used to form the hole-injecting layer 111, a phthalocyanine-based compound such as phthalocyanine (abbreviation: H$_2$Pc) or copper phthalocyanine (CuPc), a high molecular material such as poly (ethylenedioxythiophene)/poly (styrenesulfonic acid) solution (PEDOT/PSS), and the like can be given. Note that, in a case of forming the hole-injecting layer 111 with these substances, it is preferable to form the first electrode 101 using a substance having a high work function such as indium tin oxide.

In addition, the electron-injecting layer 115 may be provided between the second electrode 102 and the electron-transporting layer 114 as shown in FIG. 1. Here, the electron-injecting layer 115 is a layer having a function of assisting electrons to be injected to the electron-transporting layer 114 from the second electrode 102. By providing the electron-injecting layer 115, electron affinity difference between the second electrode 102 and the electron-transporting layer 114 is relieved; thus, electrons are easily injected. The electron-injecting layer 115 is preferably formed using a substance of which electron affinity is higher than that of a substance forming the electron-transporting layer 114 and lower than that of a substance forming the second electrode 102 or using a substance of which energy band curves by being provided as a thin film of 1 nm to 2 nm between the electron-transporting layer 114 and the second electrode 102.

In other words, the electron-injecting layer 115 can be formed by selecting a substance having relatively higher electron affinity than that of the electron-transporting layer 114. The following can be given as a specific example of a substance that can be used to form the electron-injecting layer 115: inorganic material such as alkaline metal, alkaline earth metal, fluoride of alkaline metal, fluoride of alkaline earth metal, oxide of alkaline metal, or oxide of alkaline earth metal. In addition to the inorganic material, a substance that can be used to form the electron-transporting layer 114 such as BPhen, BCP, p-EtTAZ, TAZ, or BzOs can also be used as a substance for forming the electron-injecting layer 115 by selecting a substance of which electron affinity is higher than that of a substance for forming the electron-transporting layer 114 from these substances. Note that, in a case of forming the electron-injecting layer 115 with these substances, it is preferable to form the first electrode 101 using a substance having a low work function such as aluminum.

In a light-emitting element according to the present invention described above, each of the hole-injecting layer 111, the hole-transporting layer 112, the light-emitting layer 113, the electron-transporting layer 114, and the electron-injecting layer 115 may be formed by any of an evaporation method, an ink jet method, a coating method, and the like. In addition, the first electrode 101 or the second electrode 102 may be formed by any of a sputtering method, an evaporation method, and the like.

Moreover, a hole-generating layer may be provided instead of the hole-injecting layer 111 or an electron-generating layer may be provided instead of the electron-injecting layer 115. By providing a hole-generating layer or an electron-generating layer, a light-emitting element where there is extremely small voltage increase depending on a thickness of the layers can be manufactured.

Here, the hole-generating layer is a layer for generating holes. The hole-generating layer can be formed by mixing at least one substance selected from a substance having higher mobility of holes than that of electrons and a bipolar substance with a substance that shows electron acceptability to these substances. Here, as for the substance having higher mobility of holes than that of electrons, the same substance as the substance that can be used to form the hole-transporting layer 112 can be used. Moreover, as for the bipolar substance, the above bipolar substance such as TPAQn can be used. It is preferable to particularly use a substance having a triphenylamine structure in a skeleton among the substance having higher mobility of holes than that of electrons and the bipolar substance. Holes can be generated more easily by using the substance having a triphenylamine structure in a skeleton. Further, as for the substance that shows electron acceptability, it is preferable to use metal oxide such as molybdenum oxide, vanadium oxide, ruthenium oxide, or rhenium oxide.

Further, the electron-generating layer is a layer for generating electrons. The electron-generating layer can be formed by mixing at least one substance selected from a substance having higher mobility of electrons than that of holes and a bipolar substance with a substance that shows electron-donating properties to these substances. Here, as for the substance having higher mobility of electrons than that of holes, the same substance as the substance that can be used to form the electron-transporting layer 114 can be used. Moreover, as for the bipolar substance, the above bipolar substance such as TPAQn can be used. Further, as for the substance that shows electron-donating properties, a substance selected from an alkaline metal group and an alkaline earth metal group, specifically lithium (Li), calcium (Ca), sodium (Na), potassium (K), magnesium (Mg), or the like can be used. In addition, at least one substance of alkaline metal oxide, alkaline earth metal oxide, alkaline metal nitride, alkaline earth metal nitride, and the like, specifically lithium oxide (Li$_2$O), calcium oxide (CaO), sodium oxide (Na$_2$O), potassium oxide (K$_2$O), and magnesium oxide (MgO) can also be used as the substance that shows electron-donating properties. Moreover, alkaline metal fluoride or alkaline earth metal fluoride, specifically fluoride such as lithium fluoride (LiF), cesium fluoride (CsF), or calcium fluoride (CaF$_2$) can also be used as the substance that shows electron-donating properties.

Note that, in the light-emitting element according to the present invention as described above, it is arbitrary whether to provide other layers that are different from a light-emitting layer, specifically, a hole-injecting layer, a hole-transporting layer, an electron-transporting layer, an electron-injecting layer, or the like, and it is preferably selected by a practitioner of the present invention. However, when a hole-transporting layer or an electron-transporting layer is provided, an advantageous effect of reducing the generation of quenching due to metal contained in an electrode, a hole-injecting layer, an electron-injecting layer, or the like can be obtained. In addition, an advantageous effect that electrons or holes can be efficiently injected from an electrode can be obtained by providing an electron-injecting layer, a hole-injecting layer, or the like.

Embodiment Mode 3

A light-emitting element according to the present invention using an organometallic complex according to the present invention as a light-emitting substance can emit light efficiently; therefore, light can be emitted with a few amount of current. Therefore, a light-emitting device according to the present invention using a light-emitting element according to the present invention as a pixel operates with low power consumption. This embodiment mode will explain a circuit configuration and a driving method of a light-emitting device having a display function with reference to FIGS. 2 to 5.

Figure 2:
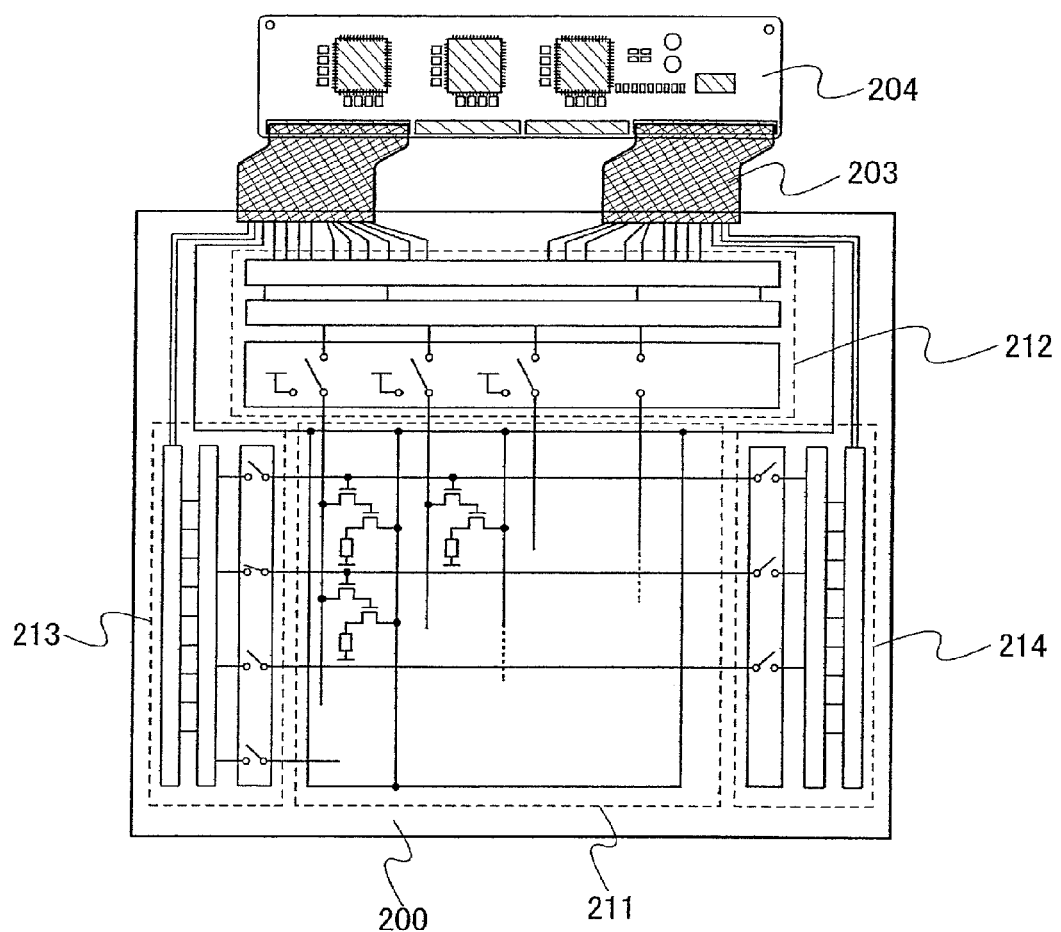
FIG. 2 is a diagram explaining a light-emitting device to which the present invention is applied.

FIG. 2 is an overhead schematic view of a light-emitting device according to this embodiment mode. In FIG. 2, a pixel portion 211, a signal line driver circuit 212, a writing scanning line driver circuit 213, and an erasing scanning line driver circuit 214 are provided over a substrate 200. Each of the signal line driver circuit 212, the writing scanning line driver circuit 213, and the erasing scanning line driver circuit 214 is connected to an FPC (flexible printed circuit) 203 that is an external input terminal through a group of wirings. In addition, each of the signal line driver circuit 212, the writing scanning line driver circuit 213, and the erasing scanning line driver circuit 214 receives signals such as a video signal, a clock signal, a start signal, and a reset signal from the FPC 6503. Moreover, a printed wiring board (PWB) 204 is attached to the FPC 203. Note that it is not always necessary to provide the driver circuit portion over one substrate over which the pixel portion 211 is provided as described above. For example, the driver circuit portion may be provided outside the substrate by using a TCP that has an IC chip over an FPC over which a wiring pattern is formed.

In the pixel portion 211, a plurality of signal lines extending in columns is arranged in rows, current-supply lines are arranged to line in rows, and a plurality of scanning lines extending in rows is arranged to line in columns. Further, in the pixel portion 211, a plurality of circuits each including a light-emitting element is arranged.

Figure 3:
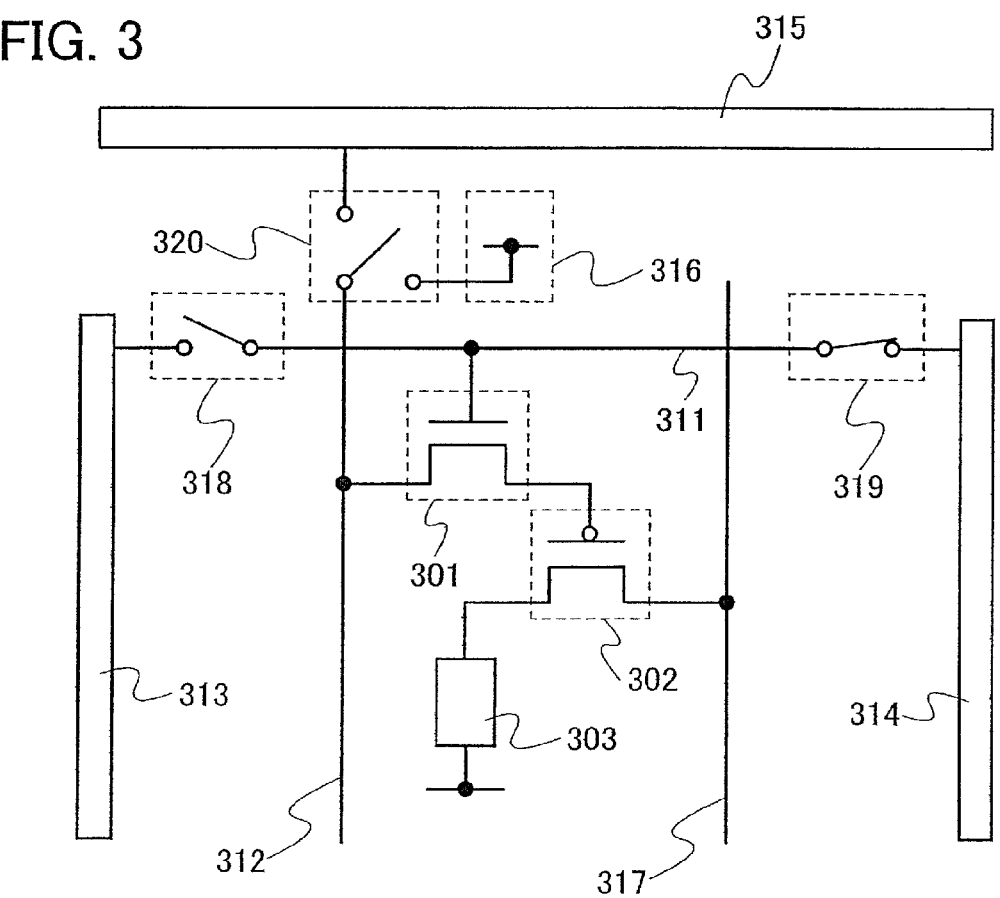
FIG. 3 is a diagram explaining a circuit included in a light-emitting device to which the present invention is applied.

FIG. 3 is a diagram showing a circuit for operating one pixel. The circuit shown in FIG. 3 includes a first transistor 301, a second transistor 302, and a light-emitting element 303.

Each of the first transistor 301 and the second transistor 302 is a three-terminal element including a gate electrode, a drain region, and a source region, and including a channel region between the drain region and the source region. Here, a source region and a drain region are switched with each other in accordance with a structure, operating conditions, or the like of a transistor; therefore, it is difficult to identify which one is the source region or the drain region. Consequently, regions that serve as a source or a drain are respectively referred to as a first electrode of a transistor and a second electrode of a transistor in this embodiment mode.

A scanning line 311 and a writing scanning line driver circuit 313 are provided so as to be electrically connected or unconnected by a switch 318, the scanning line 311 and an erasing scanning line driver circuit 314 are provided so as to be electrically connected or unconnected by a switch 319, and a signal line 312 is provided so as to be electrically connected to either a signal line driver circuit 315 or a power source 316 by a switch 320. Further, the first transistor 301 has a gate electrically connected to the scanning line 311, a first electrode electrically connected to the signal line 312, and a second electrode electrically connected to a gate electrode of the second transistor 302. The second transistor 302 has a first electrode electrically connected to a power supply line 317 and a second electrode electrically connected to one electrode included in the light-emitting element 303. Note that the switch 318 may be included in the writing scanning line driver circuit 313, the switch 319 may be included in the erasing scanning line driver circuit 314, and the switch 320 may be included in the signal line driver circuit 315. Note that a capacitor element may be provided between the gate of the second transistor 302 and the power supply line.

Figure 4:
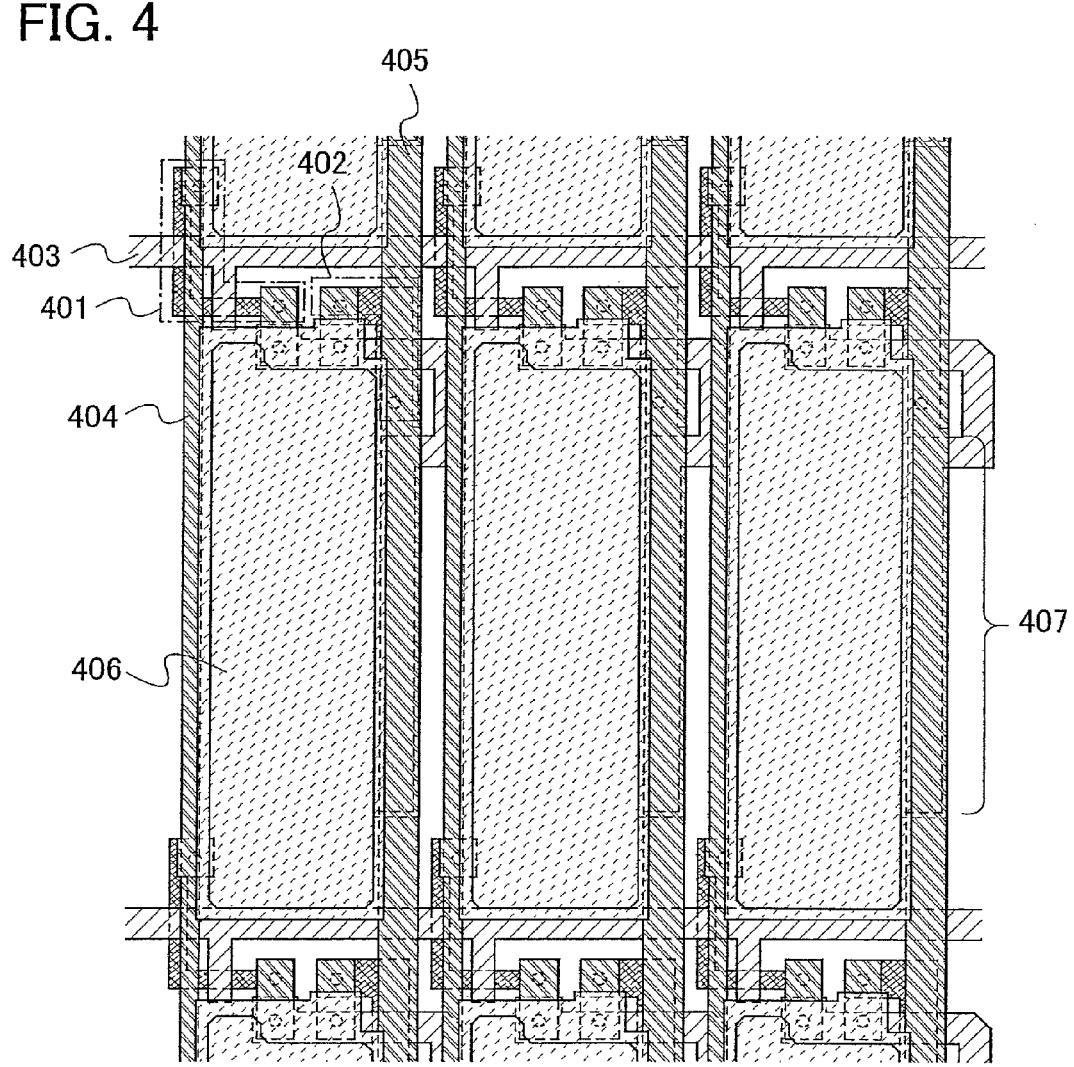
FIG. 4 is a top view of a light-emitting device to which the present invention is applied.

In addition, arrangement of a transistor, a light-emitting element, and the like in a pixel is not particularly limited. For example, arrangement shown in a top view of FIG. 4 can be employed. In FIG. 4, a first transistor 401 has a first electrode connected to a signal line 404 and a second electrode connected to a gate electrode of a second transistor 402. In addition, the second transistor 402 has a first electrode connected to a power supply line 405 and a second electrode connected an electrode 406 of a light-emitting element. Part of a scanning line 403 serves as a gate electrode of the first transistor 401. A region 407 where a gate wiring of the second transistor 402 is overlapped with the power supply line 405 serves as a capacitor element.

Next, a driving method will be explained. FIG. 5 is a diagram explaining operation per frame with time. In FIG. 5, the horizontal direction indicates passage of time, and the vertical direction indicates ordinal numbers of scanning lines.

When a light-emitting device according to the present invention is used to display images, rewrite operation and display operation for a screen are repeated in a display period. Although the number of rewrites is not particularly limited, it is preferable that the number of rewrites be about 60 times per second so as not to make an image viewer recognize flickers. Here, a period for which rewrite operation and display operation are performed for a screen (one frame) is referred to as one frame period.

As shown in FIG. 5, one frame is divided into four sub-frames 501, 502, 503, and 504 respectively including writing periods 501a, 502a, 503a, and 504a and retention periods 501b, 502b, 503b, and 504b. In the retention period, a light-emitting element to which a signal for emitting light is given is made to be in an emitting state. The ratio of the length of the retention period in each sub-frame is first sub-frame 501 to second sub-frame 502 to third sub-frame 503 to fourth sub-frame 504 is $2^3:2^2:2^1:2^0=8:4:2:1$. This makes 4-bit gradation possible. However, the number of bits or the number of gradations is not limited to that described here. For example, eight sub-frames may be provided so as to perform 8-bit gradation.

Operation in one frame will be explained. First, in the sub-frame 501, writing operation is sequentially performed for each of the first row to the last row. Accordingly, the start time of the writing period 501a is different depending on the row. When the writing period 501a is completed, the row is sequentially moved into the retention period 501b. In the retention period 501b, a light-emitting element to which a signal for emitting light is given is made to be in an emitting state. In addition, when the retention period 501b is completed, the row is sequentially moved into the next sub-frame 502, and writing operation is sequentially performed for each of the first row to the last row as in the case of the sub-frame 501. The operation described above is repeated to complete the retention period 504b of the sub-frame 504. When the operation in the sub-frame 504 is completed, the row is moved into the next frame. Thus, the total of time for which light is emitted in each sub-frame is emission time for each light-emitting element in one frame. By varying this emission time with respect to each light-emitting element to have various combinations in one pixel, various different display colors in luminosity and chromaticity can be made.

As in the sub-frame 504, when forcible termination of a retention period of a row for which writing is already completed to move into the retention time is required before writing for the last row is completed, it is preferable that an erasing period 504c is provided after the retention period 504b and a row is controlled so as to be in a non-emitting state forcibly. In addition, the row made to be in the non-emitting state forcibly is kept the non-emitting state for a certain period (this period is referred to as a non-emission period 504d). Then, immediately after the writing period 504a of the last row is completed, the rows are sequentially moved into the next writing period (or the next frame), starting from the first row. This makes it possible to prevent the writing period 504a of the sub-frame 504 from overlapping with the writing period of the next sub-frame.

Although the sub-frames 501 to 504 are arranged in the order of retention period from longest to shortest in this embodiment mode, the arrangement as in this embodiment mode is not always necessary. For example, the sub-frames 501 to 504 may be arranged in the order of retention period from shortest to longest, or may be arranged in random order. In addition, the sub-frames may be divided further into a plurality of frames. In other words, scanning of the gate signal lines may be performed more than once while giving the same image signal.

Now, operation of the circuit shown in FIG. 3 in a writing period and an erasing period will be explained.

First, operation in a writing period will be explained. In the writing period, the n-th (n is a natural number) scanning line 311 is electrically connected to the writing scanning line driver circuit 313 through the switch 318, and unconnected to the erasing scanning line driver circuit 314. In addition, the signal line 312 is electrically connected to the signal line driver circuit 315 through the switch 320. In this case, a signal is inputted into the gate of the first transistor 301 connected to the n-th (n is a natural number) scanning line 311 to turn on the first transistor 301. Then, at this moment, image signals are inputted simultaneously into the first to last signal lines 312. Note that the image signals inputted from the respective signal lines 312 are independent of each other. The image signal inputted from each of the signal lines 312 is inputted into the gate electrode of the second transistor 302 through the first transistor 301 connected to the signal line 312. At this moment, whether the light-emitting element 303 emits light or not depends on the signal inputted into the second transistor 302. For example, when the second transistor 302 is a P-channel type, the light-emitting element 303 is made to emit light by inputting a Low Level signal to the gate electrode of the second transistor 302. On the other hand, when the second transistor 302 is an N-channel type, the light-emitting element 303 is made to emit light by inputting a High Level signal to the gate electrode of the second transistor 302.

Next, operation in an erasing period will be explained. In the erasing period, the n-th (n is a natural number) scanning line 311 is electrically connected to the erasing scanning line driver circuit 314 through the switch 319 and unconnected to the wiring scanning line driver circuit 313. In addition, the signal line 312 is electrically connected to the power source 316 through the switch 320. In this case, a signal is inputted into the gate of the first transistor 301 connected to the n-th (n is a natural number) scanning line 311 to turn on the first transistor 301. Then, at this moment, erasing signals are inputted simultaneously into the first to last signal lines 312. The erasing signal inputted from each of the signal lines 312 is inputted into the gate electrode of the second transistor 302 through the first transistor 301 connected to the signal line 312. At this moment, current supply from the power supply line 317 to the light-emitting element 303 is blocked in accordance with the signal inputted into the second transistor 302. Then, the light-emitting element 303 is forcibly made to be in a non-emitting state. For example, when the second transistor 302 is a P-channel type, the light-emitting element 303 is made to emit no light by inputting a High Level signal to the gate electrode of the second transistor 302. On the other hand, when the second transistor 302 is an N-channel type, the light-emitting element 303 is made to emit no light by inputting a Low Level signal to the gate electrode of the second transistor 302.

Note that, as for the n-th row (n is a natural number), signals for erasing are inputted by the operation as described above in an erasing period. However, as described above, the other row (referred to as the m-th row (m is a natural number)) may be in a writing period while the n-th row is in an erasing period. In such a case, it is necessary to input a signal for erasing into the n-th row and input a signal for writing into the m-th row by using the same source signal line. Therefore, operation explained below is preferable.

Immediately after the n-th light-emitting element 303 is made to emit no light by the operation in the erasing period explained above, the scanning line 311 and the erasing scanning line driver circuit 314 are made to be unconnected to each other, and the switch 320 is switched to connect the signal line 312 and the signal line driver circuit 315. Then, in addition to connecting the signal line 312 to the signal line driver circuit 315, the scanning line 311 is connected to the writing scanning line driver circuit 313. Then, a signal is inputted selectively into the m-th signal line from the writing scanning line driver circuit 313 to turn on the first transistor 301, and signals for writing are inputted into the first to last signal lines 312 from the signal line driver circuit 315. This signal makes the m-th light-emitting element 303 is made to be in an emitting or non-emitting state.

Immediately after the writing period for the m-th row is completed as described above, an erasing period for the (n+1)-th row is started. For that purpose, the scanning line 311 and the writing scanning line driver circuit 313 are made to be unconnected to each other, and the switch 320 is switched to connect the signal line 312 to the power source 316. Further, the scanning line 311, which is unconnected to the writing scanning line driver circuit 313, is made to be connected to the erasing scanning line driver circuit 314. Then, a signal is inputted selectively into the (n+1)-th scanning line 311 from the erasing scanning line driver circuit 314 to turn on the first transistor 301, and an erasing signal is inputted from the power source 316. Immediately after the erasing period for the (n+1)-th row is thus completed, a writing period for the m-th row is started. Hereinafter, an erasing period and a writing period may be repeated in the same way until an erasing period for the last row is completed.

Although this embodiment mode explains the mode in which the writing period for the m-th row is provided between the erasing period for the n-th row and the erasing period for the (n+1)-th row, the present invention is not limited thereto. The writing period for the m-th row may be provided between an erasing period for (n−1)-th row and an erasing period for n-th row.

In addition, in this embodiment mode, the operation in which the erasing scanning line driver circuit 314 and one scanning line 311 are made to be unconnected to each other and the writing scanning line driver circuit 313 and the other gate scanning line 311 are made to be connected to each other is repeated as the non-emission period 504d is provided in the sub-frame 504. This type of operation may be performed in a frame in which a non-emission period is not particularly provided.

Embodiment Mode 4

One mode of a cross-sectional view of a light-emitting device including a light-emitting element according to the present invention will be explained with reference to FIGS. 6A to 6C.

Figure 6A:
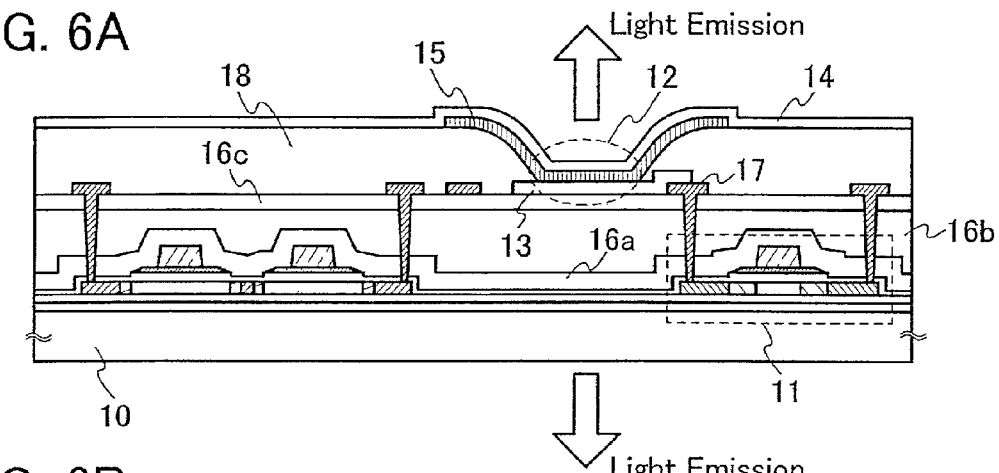
FIGS. 6A to 6C are cross-sectional views of a light-emitting device to which the present invention is applied.
Figure 6B:
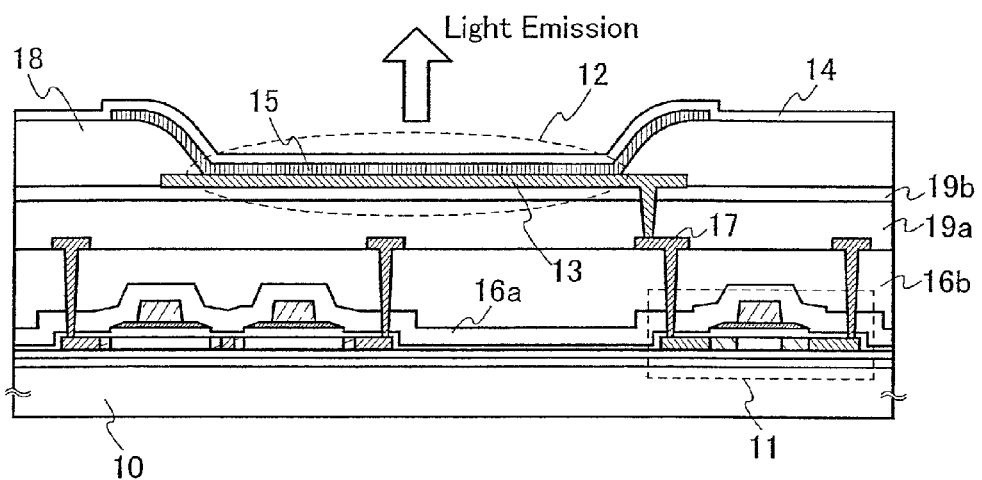
Figure 6C:
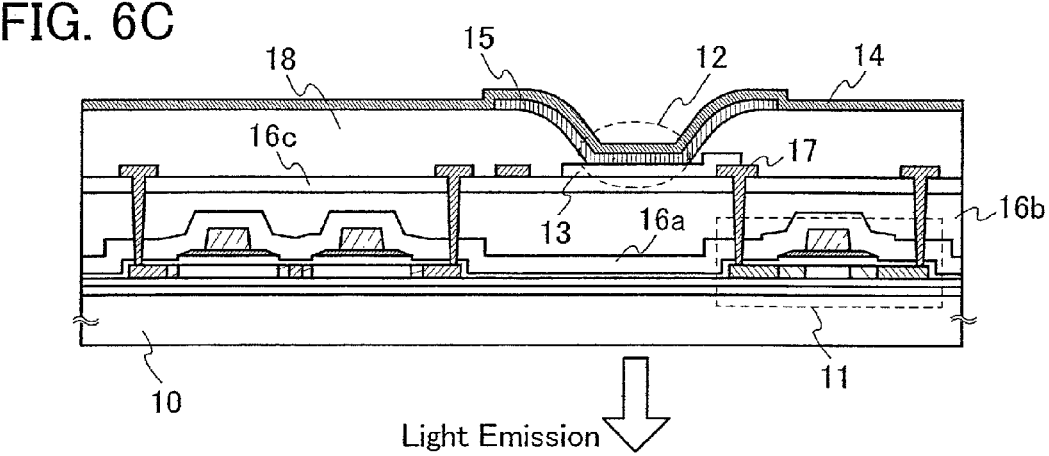

In each of FIGS. 6A to 6C, a rectangular portion surrounded by a dotted line is a transistor 11 provided for driving a light-emitting element 12 according to the present invention. The light-emitting element 12 is a light-emitting element according to the present invention, which has a layer 15 in which a layer for generating holes, a layer for generating electrons, and a layer containing a light-emitting substance are stacked between a first electrode 13 and a second electrode 14. A drain of the transistor 11 and the first electrode 13 are electrically connected to each other by a wiring 17 running through a first interlayer insulating film 16 (16a, 16b, and 16c). In addition, the light-emitting element 12 is separated by a partition layer 18 from another light-emitting element provided adjacently. A light-emitting device having such a structure according to the present invention is provided over a substrate 10 in this embodiment mode.

Note that the transistor 11 shown in each of FIGS. 6A to 6C is a top-gate TFT in which a gate electrode is provided on the opposite side of a substrate as a center from a semiconductor layer. However, the structure of the transistor 11 is not particularly limited. For example, a bottom-gate type may also be used. In the case of a bottom-gate TFT, a TFT where a protective film is formed over a semiconductor layer that forms a channel (a channel-protected type) may be employed, or a TFT where part of a semiconductor layer that forms a channel is concave (a channel-etched type) may be employed.

In addition, a semiconductor layer for forming the transistor 11 may be either crystalline or amorphous, or alternatively, may be microcrystal or the like.

The following will describe a microcrystal semiconductor. The microcrystal semiconductor is a semiconductor that has an intermediate structure between amorphous and crystalline (such as single-crystal or polycrystalline) structures and has a third state that is stable in terms of free energy, which includes crystalline region that has short range order and lattice distortion. Further, a crystal grain from 0.5 to 20 nm is included in at least a region in a film. Raman spectrum of the microcrystal semiconductor is shifted to a lower wavenumber side less than 520 cm$^{-1}$. The diffraction peaks of (111) and (220), which are believed to be derived from silicon crystal lattice, are observed in the microcrystal semiconductor by the X-ray diffraction. The microcrystal semiconductor contains hydrogen or halogen of at least 1 atomic % or more for terminating dangling bonds. The microcrystal semiconductor is formed by glow discharge decomposition with a gas such as $SiH_4$, $Si_2H_6$, $SiH_2Cl_2$, $SiHCl_3$, $SiCl_4$, or $SiF_4$ (using plasma CVD). Each of these gases may also be diluted with $H_2$, or a mixture of $H_2$ and one or more of rare gas elements of He, Ar, Kr, and Ne. The dilution ratio is set to be in the range of 1:2 to 1:1,000. The pressure is set to be approximately in the range of 0.1 to 133 Pa. The power frequency is set to be 1 to 120 MHz, preferably, 13 to 60 MHz. The substrate heating temperature is set to be 300° C. or less, preferably, 100 to 250° C. As for impurity elements contained in the film, each concentration of impurities for atmospheric constituents such as oxygen, nitrogen, and carbon is preferably set to be $1\times10^{20}/cm^3$ or less. In particular, the oxygen concentration is set to be $5\times10^{19}/cm^3$ or less, preferably, $1\times10^{19}/cm^3$ or less.

Moreover, specific examples of crystalline semiconductors for the semiconductor layer include single-crystal or polycrystalline silicon and silicon-germanium, which may be formed by laser crystallization or may be formed by crystallization with solid-phase growth using an element such as nickel.

In a case of using an amorphous substance, for example, amorphous silicon to form the semiconductor layer, it is preferable that the light-emitting device have a circuit in which the transistor 11 and the other transistor (a transistor forming the circuit for driving the light-emitting element) are all N-channel transistors. Other than that case, the light-emitting device may have a circuit including one of an N-channel transistor and a P-channel transistor or may have a circuit including both an N-channel transistor and a P-channel transistor.

Further, the first interlayer insulating film 16 may be a multilayer as shown in FIG. 6A, 6B, and 6C, or may be a single layer. Note that the first interlayer insulating film 16a includes an inorganic material such as silicon oxide or silicon nitride, and the first interlayer insulating film 16b includes a substance with self-flatness such as acrylic, siloxane (note that a siloxane resin corresponds to a resin including a Si—O—Si bond. Siloxane has a framework structure formed by the bond between silicon (Si) and oxygen (O). As a substituent, an organic group including at least hydrogen (for example, an alkyl group or an aromatic hydrocarbon group) is used. As a substituent, a fluoro group may also be used, or an organic group including at least hydrogen and a fluoro group may also be used), or silicon oxide that can be formed by being coated. Furthermore, the first interlayer insulating film 16c has a silicon nitride film containing argon (Ar). Note that the substances included in the respective layers are not particularly limited; therefore, substances other than the substances mentioned here may be used. Moreover, a layer including a substance other than these substances may be combined. In such a manner, both an inorganic material and an organic material, or one of an inorganic material and an organic material may be used to form the first interlayer insulating film 16.

As for the partition layer 18, it is preferable that an edge portion have a shape varying continuously in curvature radius. In addition, acrylic, siloxane, resist, silicon oxide, or the like is used to form the partition layer 18. Either an inorganic material or an organic material, or both may be used to form the partition layer 18.

In each of FIGS. 6A and 6C, only the first interlayer insulating film 16 is provided between the transistor 11 and the light-emitting element 12. However, as shown in FIG. 6B, a second interlayer insulating film 19 (19a and 19b) may be provided in addition to the first interlayer insulating film 16 (16a and 16b). In the light-emitting device shown in FIG. 6B, the first electrode 13 is connected to the wiring 17 through the second interlayer insulating film 19.

The second interlayer insulating film 19 may be a multi-layer or a single layer in the same way as the first interlayer insulating film 16. The second interlayer insulating film 19a includes a substance with self-flatness such as acrylic, siloxane, or silicon oxide that can be formed by being coated. In addition, the second interlayer insulating film 19b has a silicon nitride film including argon (Ar). The substances included in the respective layers are not particularly limited; therefore, substances other than the substances mentioned here may be used. Moreover, a layer including a substance other than these substances may be combined. In such a manner, both an inorganic material and an organic material, or one of an inorganic material and an organic material may be used to form the second interlayer insulating film 19.

In the light-emitting element 12, in a case where both the first electrode 13 and the second electrode 14 are formed by using a light-transmitting substance, emitted light can be extracted from both the first electrode 13 side and the second electrode 14 side as indicated by outline arrows of FIG. 6A. In a case where only the second electrode 14 is formed by using a light-transmitting material, emitted light can be extracted from only the second electrode 14 side as indicated by an outline arrow of FIG. 6B. In this case, it is preferable that the first electrode 13 include a highly reflective material or that a film composed of a highly reflective material (a reflective film) be provided below the first electrode 13. In a case where only the first electrode 13 is formed by using a light-transmitting substance, emitted light can be extracted from only the first electrode 13 side as indicated by an outline arrow of FIG. 6C. In this case, it is preferable that the second electrode 14 include a highly reflective material or that a reflective film be provided above the second electrode 14.

In addition, the layer 15 may be stacked so that the light-emitting element 12 operates when a voltage is applied so that the potential of the second electrode 14 gets higher than the potential of the first electrode 13, or the layer 15 may be stacked so that the light-emitting element 12 operates when a voltage is applied so that the potential of the second electrode 14 gets lower than the potential of the first electrode 13. The transistor 11 is an N-channel transistor in the former case, and the transistor 11 is a P-channel transistor in the latter case.

As described above, an active light-emitting device in which driving of a light-emitting element is controlled by a transistor is explained in this embodiment mode. However, without limitation to an active light-emitting device, the present invention may be applied to a passive light-emitting device.

Figure 7:
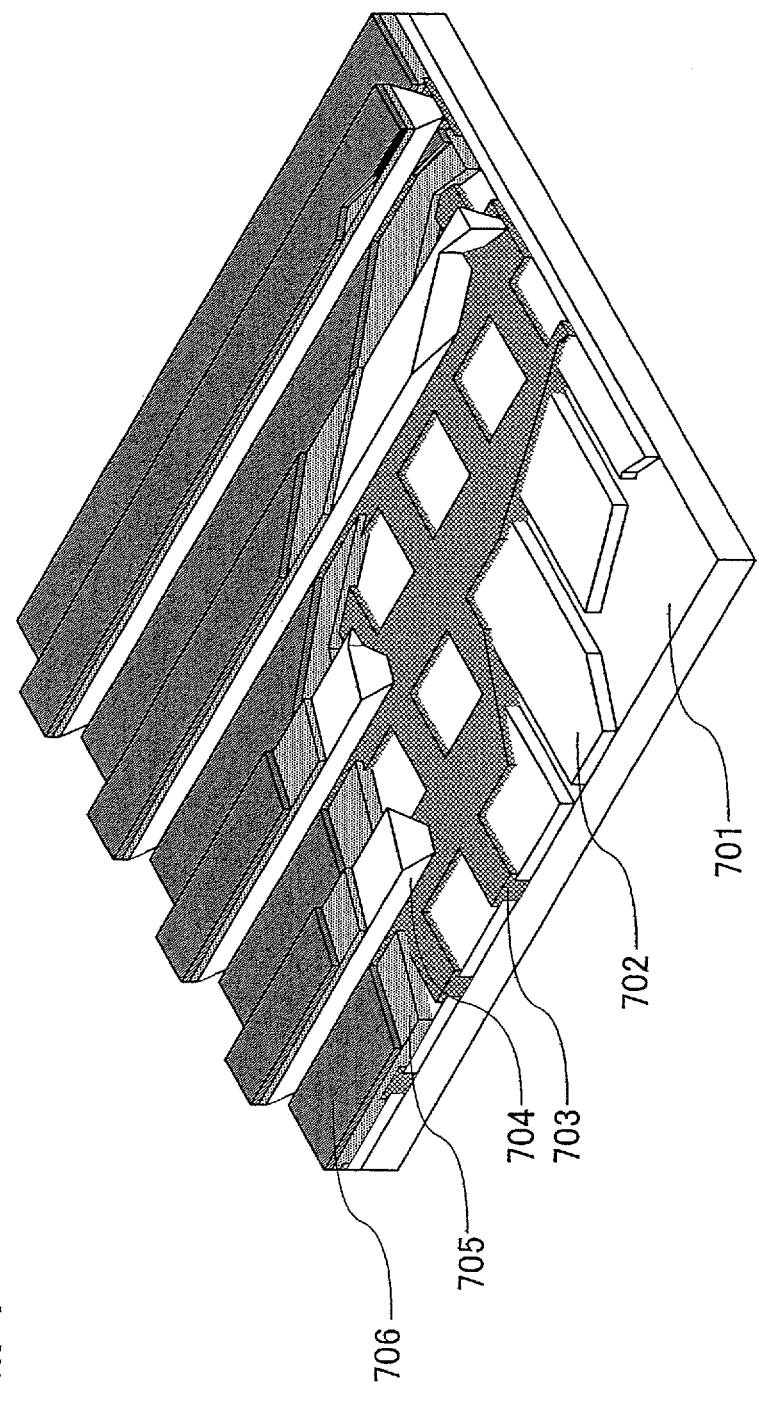
FIG. 7 is a view explaining a light-emitting device to which the present invention is applied.

FIG. 7 shows a perspective view of a passive light-emitting device to which the present invention is applied. In FIG. 7, a layer 705 where a layer containing a light-emitting substance, a layer for generating electrons, and a layer for generating holes are sequentially stacked is provided between an electrode 702 and an electrode 706 over a substrate 701. The end of the electrode 702 is covered with an insulating layer 703. A partition layer 704 is provided over the insulating layer 703. The nearer the sidewall of the partition layer is to a substrate surface, the narrower the distance between one sidewall and the other sidewall is to have inclination. In other words, a cross section of the partition layer 704 in a minor axis is a trapezoid, in which the lower base (a base in the same direction as the face direction of the insulating layer 703 and in contact with the insulating layer 703) is shorter than the upper base (a base in the same direction as the face of the insulating layer 703 and not in contact with the insulating layer 703). Accordingly, defectiveness of a light-emitting element due to static electricity or the like can be prevented by providing the partition layer 704. In addition, a passive light-emitting device can also be driven with low power consumption by including a light-emitting element according to the present invention that is operated with a low drive voltage.

Since a light-emitting element according to the present invention using an organometallic complex according to the present invention as a light-emitting substance emits light efficiently, active and passive light-emitting devices according to the present invention each using a light-emitting element according to the present invention as a pixel operate with low power consumption. Note that, in the case of the active light-emitting device, a light-emitting element having high luminous efficiency can be obtained by using an organometallic complex according to the present invention for G (green) or B (blue), and using a known phosphorescent material for R (red) among pixels of R (red), G (green), and B (blue). Therefore, the active light-emitting device according to the present invention using this light-emitting element as a pixel can operate with low power consumption.

Embodiment Mode 5

Since a light-emitting device including a light-emitting element according to the present invention can operate with low power consumption, an electronic device with low power consumption can be obtained by the present invention.

Figure 8A:
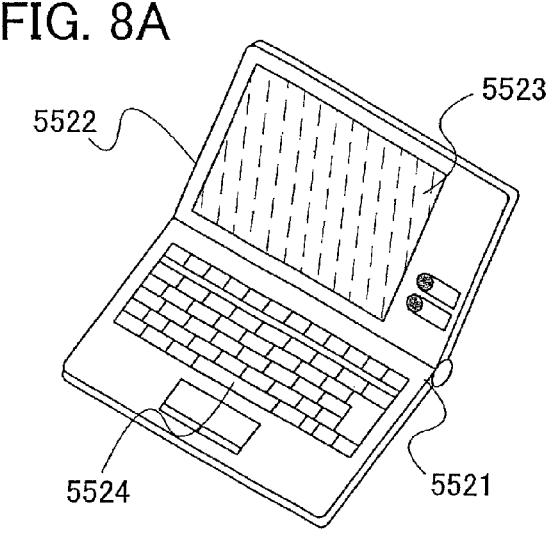
FIGS. 8A to 8C are views of electronic devices to which the present invention is applied.
Figure 8B:
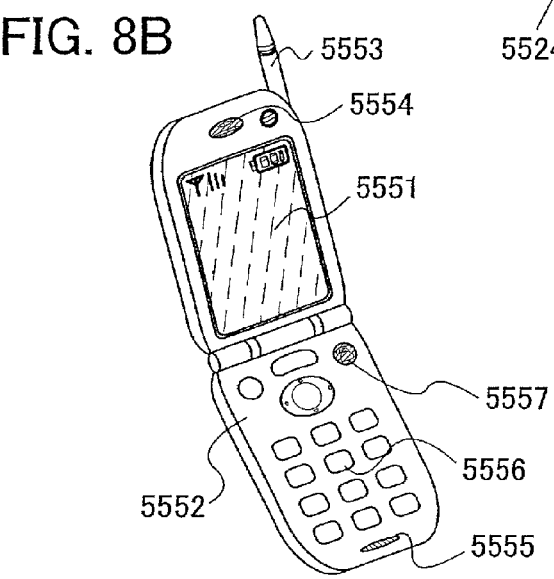
Figure 8C:
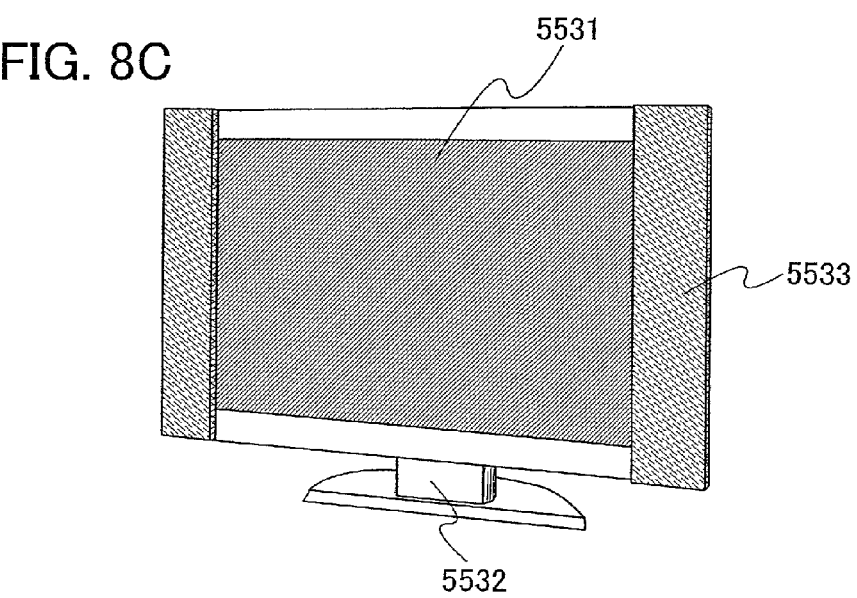

Each of FIGS. 8A to 8C shows one embodiment of an electronic device mounted with a light-emitting device to which the present invention is applied.

FIG. 8A is a computer manufactured by applying the present invention, which includes a main body 5521, a housing 5522, a display portion 5523, a keyboard 5524, and the like. A light-emitting device where light-emitting elements using, as a light-emitting substance the organometallic complex according to the present invention, which is explained in Embodiment Modes 1 and 2, are arranged in matrix is incorporated into the display portion 5523. In such a manner, the personal computer can be completed by incorporating a light-emitting device having a light-emitting element containing the organometallic complex according to the present invention as the display portion. Since the display portion of such a personal computer can emit light efficiently, power consumption can be reduced.

FIG. 8B is a telephone hand set manufactured by applying the present invention, in which a main body 5552 includes a display portion 5551, an audio output portion 5554, an audio input portion 5555, operation switches 5556 and 5557, an antenna 5553, and the like. A light-emitting device where light-emitting elements using, as a light-emitting substance the organometallic complex according to the present invention, which is explained in Embodiment Modes 1 and 2, are arranged in matrix is incorporated into the display portion 5551. In such a manner, the telephone hand set can be completed by incorporating a light-emitting device having a light-emitting element containing the organometallic complex according to the present invention as the display portion. Since the display portion of such a telephone handset can emit light efficiently, power consumption can be reduced.

FIG. 8C is a television receiver manufactured by applying the present invention, which includes a display portion 5531, a housing 5532, speakers 5533, and the like. A light-emitting device where light-emitting elements using, as a light-emitting substance the organometallic complex according to the present invention, which is explained in Embodiment Modes 1 and 2, are arranged in matrix is incorporated into the display portion 5531. In such a manner, the television receiver can be completed by incorporating a light-emitting device having a light-emitting element containing an organometallic complex according to the present invention as the display portion. Since the display portion of such a television receiver can emit light efficiently, power consumption can be reduced.

As described above, a light-emitting device according to the present invention is extremely suitable to be used as the display portions of various kinds of electronic devices. Note that, although this embodiment mode describes a personal computer, a telephone hand set, and the like, a light-emitting device having a light-emitting element according to the present invention may also be mounted on a navigation device, a camera, or the like.

Embodiment 1

Synthesis Example 1

A synthesis method of an organometallic complex according to the present invention represented by a structural formula (13) (name: bis[3,5-bis(4-tert-butylphenyl)-4-phenyl-1,2,4-triazolato](picolinato)iridium(III), abbreviation: [Ir(t-Butaz)$_2$(pic)]) will be explained.

Step 1: Synthesis of Dinuclear Complex ([Ir(t-Butaz)$_2$Cl]$_2$)

First, with a mixture of 30 mL of 2-ethoxyethanol and 10 mL of water as a solvent, 2.59 g of the ligand H(t-Butaz) (3,5-bis(4-tert-butyl-phenyl)-4-phenyl-[1,2,4]triazole) [manufactured by H. W. SANDS. CORP.] and 0.76 g of iridium chloride (IrCl$_3$·H$_2$O) were mixed, and held at reflux in a nitrogen atmosphere for 14 hours to obtain a dinuclear complex [Ir(t-Butaz)$_2$Cl]$_2$ (yellow powder, yield: 53%). A synthetic scheme (a-1) according to synthesis of Step 1 is shown below.

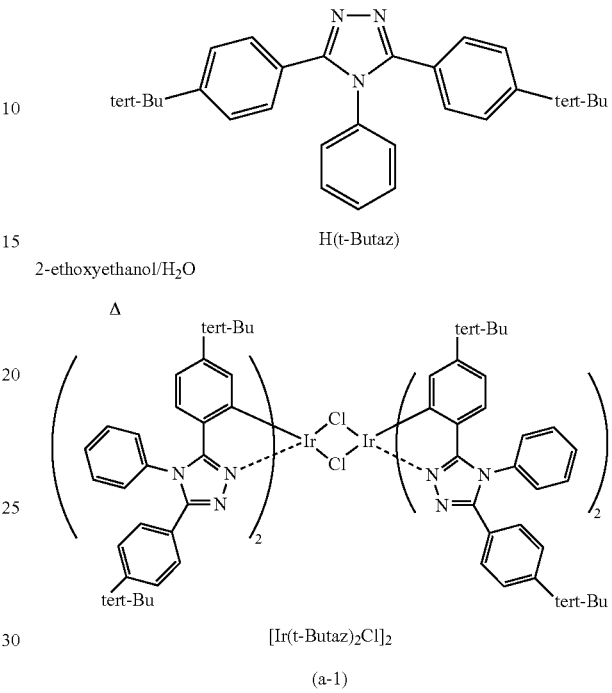

(a-1)

Step 2: Synthesis of Organometallic Complex (Abbreviation: [Ir(t-Butaz)$_2$(Pic)]) According to the Present Invention Further, with 20 mL of dichloromethane as a solvent, 0.60 g of the above obtained [Ir(t-Butaz)$_2$Cl]$_2$, 0.28 g of picolinic acid (Hpic) were mixed, and held at reflux in a nitrogen atmosphere for 18 hours. A reaction solution is concentrated and dried, and recrystallized with chloroform to obtain an organometallic complex Ir(t-Butaz)$_2$(pic) according to the present invention (a yellow crystal, yield: 72%). A synthetic scheme (a-2) according to synthesis of Step 2 is shown below.

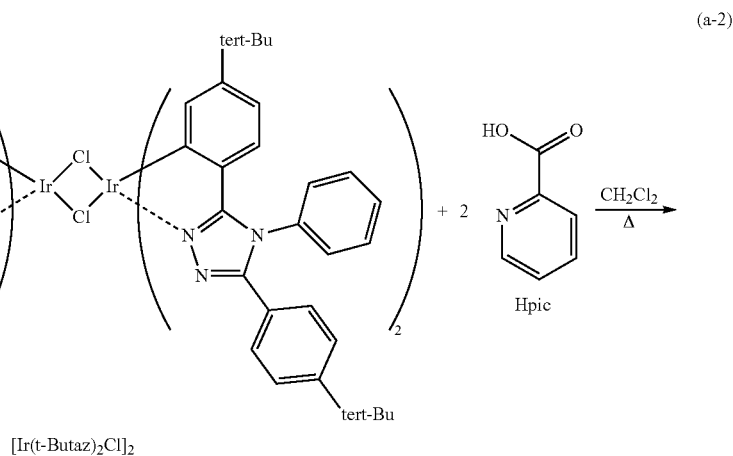

(a-2)

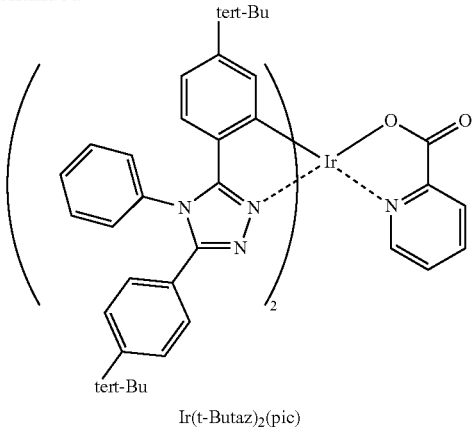

Ir(t-Butaz)₂(pic)

A result of mass spectroscopy of the obtained compound is shown below.

MS: m/z 1133 ([M+H]⁺), 1155 ([M+Na]⁺)

Figure 9:
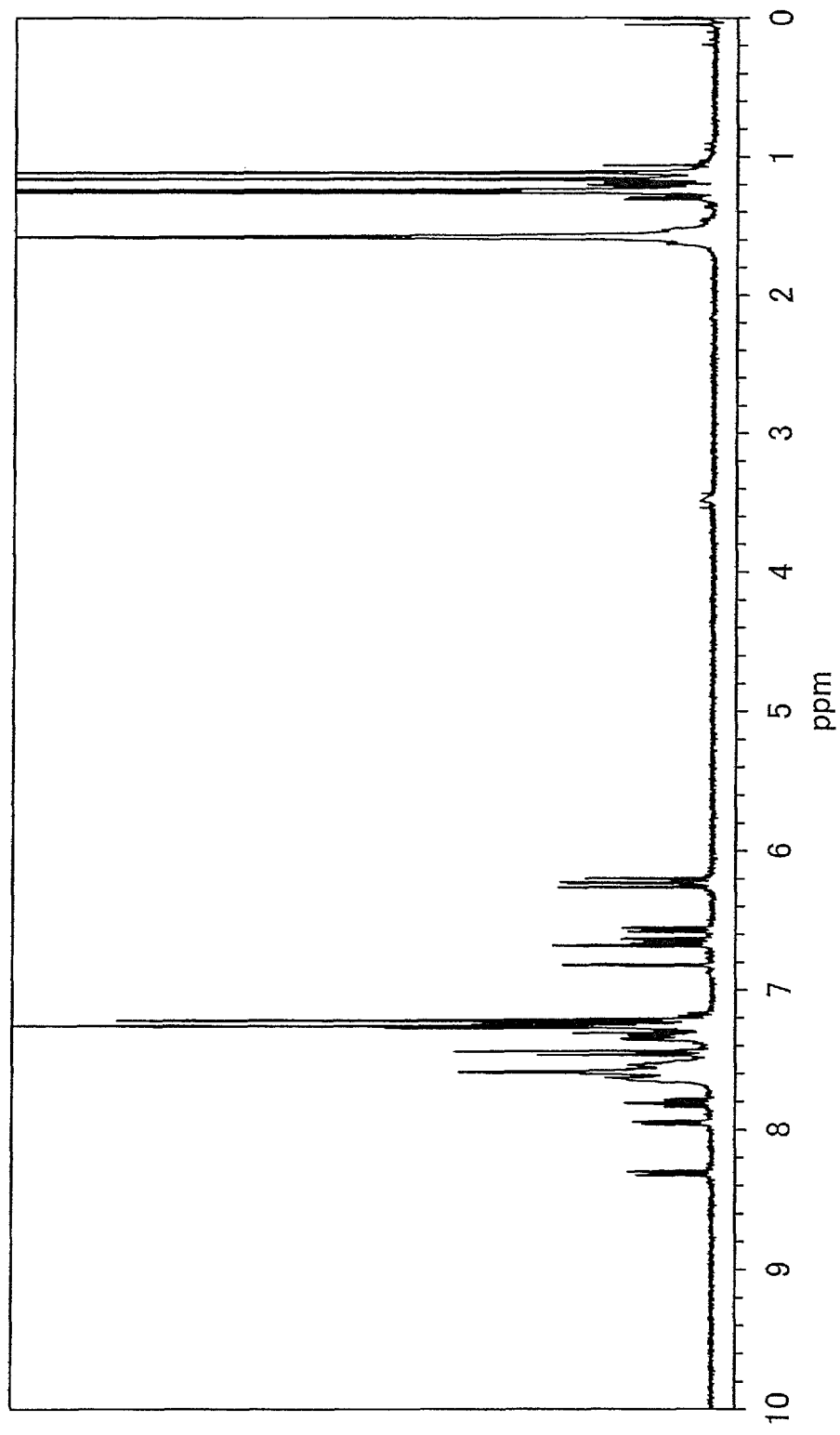
FIG. 9 is a chart obtained by analyzing an organometallic complex according to the present invention, which is synthesized in Synthesis Example 1, by $^1$H-NMR.

A result of nuclear magnetic resonance spectrometry (¹H-NMR) of the obtained compound is shown below. In addition, FIG. 9 shows a chart of ¹H-NMR.

¹H-NMR. δ (CDCl₃): 8.32 (d, 1H), 7.96 (d, 1H), 7.81 (td, 1H), 7.59 (m, 9H), 7.44 (m, 2H), 7.35-7.17 (m, 8H), 6.82 (d, 1H), 6.67 (m, 2H), 6.57 (dd, 1H), 6.27-6.20 (m, 2H), 1.26 (s, 9H), 1.24 (s, 9H), 1.16 (s, 9H), 1.12 (s, 9H).

In addition, measurement of the thermal decomposition temperature $T_d$ of the obtained organometallic complex Ir(t-Butaz)₂(pic) according to the present invention was performed by a Thermogravimetry/Differential Thermal Analysis simultaneous measurement system (manufactured by Seiko Instruments Inc., TG/DTA-320) to find $T_d$=410° C.; thus, it was found that the organometallic complex Ir(t-Butaz)₂(pic) according to the present invention shows favorable heat resistance.

Figure 10:
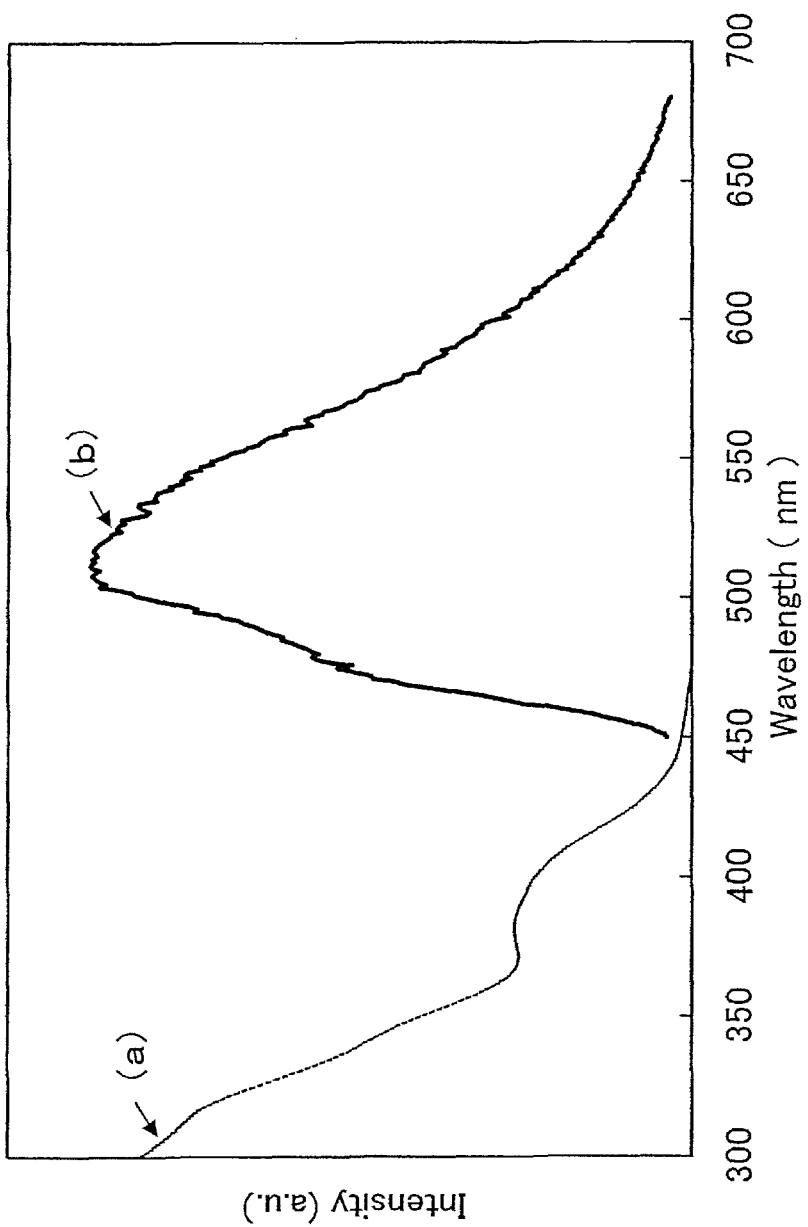
FIG. 10 is a graph showing an absorption spectrum and a light emission spectrum of an organometallic complex according to the present invention.

Moreover, FIG. 10 shows a measurement result at a room temperature of (a) an absorption spectrum and (b) an emission spectrum (PL) of Ir(t-Butaz)₂(pic) in dichloromethane. In FIG. 10, the horizontal axis indicates a wavelength (nm), and the vertical axis indicates intensity of absorption and light emission (an arbitrary unit). As is apparent from FIG. 10, the organometallic complex Ir(t-Butaz)₂(pic) according to the present invention has absorption peaks at 318 nm (sh), 348 nm (sh), 382 nm, and 450 nm (sh), and has emission peak at 509 nm and emitted green light.

In addition, light emission derived from the compound is hardly observed when a dichloromethane solution of the organometallic complex Ir(t-Butaz)₂(pic) according to the present invention is irradiated with light to dissolve oxygen, while light emission is observed in a case of dissolving argon, thereby showing the same tendency as a substance generating phosphorescence. Accordingly, it can be confirmed that light emission derived from Ir(t-Butaz)₂(pic) is phosphorescence.

Synthesis Example 2

This Synthesis Example 2 will explain a synthesis method of an organometallic complex according to the present invention represented by a structural formula 15 (name: bis[3,5-bis(4-tert-butylphenyl)-4-phenyl-1,2,4-triazolato][tetrakis(1-pyrazolyl)borato]iridium(III), abbreviation: [Ir(t-Butaz)₂(bpz₄)]).

Step 1: Synthesis of an Organometallic Complex (Abbreviation: [Ir(t-Butaz)₂(Bpz₄)]) According to the Present Invention First, 1.14 g of the dinuclear complex [Ir(t-Butaz)₂Cl]₂ obtained in Step 1 of Synthesis Example 1 was suspended in 40 ml of dichloromethane. Then, a solution, in which 0.36 g of silver trifluoromethanesulfonate was dissolved in 40 ml of a methanol solvent, was dropped to the suspension solution. Then, suspension solution was stirred at room temperature for 2 hours and further centrifuged. A supernant solution obtained by the centrifugation was divided by decantation to be concentrated and dried. Next, the solid obtained by being concentrated and dried was mixed with 0.61 g of tetrakis(1-pyrazolyl)borate potassium salt (manufactured by Acros Organics) by using 30 ml of acetonitrile as a solvent. Then, the mixed solution was held at reflux in a nitrogen atmosphere for 20 hours to obtain a yellow powder (yield: 47%). A synthetic scheme (a-2') of this synthesis is shown below.

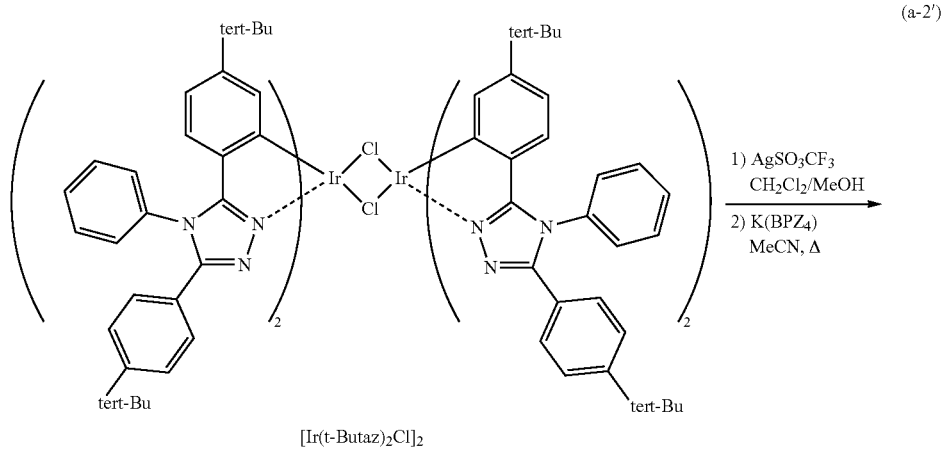

(a-2')

[Ir(t-Butaz)₂Cl]₂

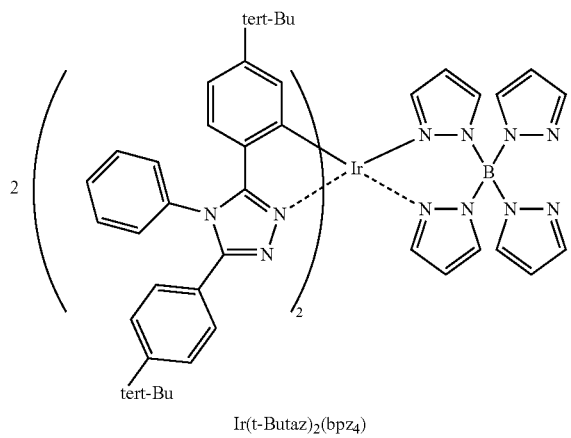

Ir(t-Butaz)₂(bpz₄)

Figure 11:
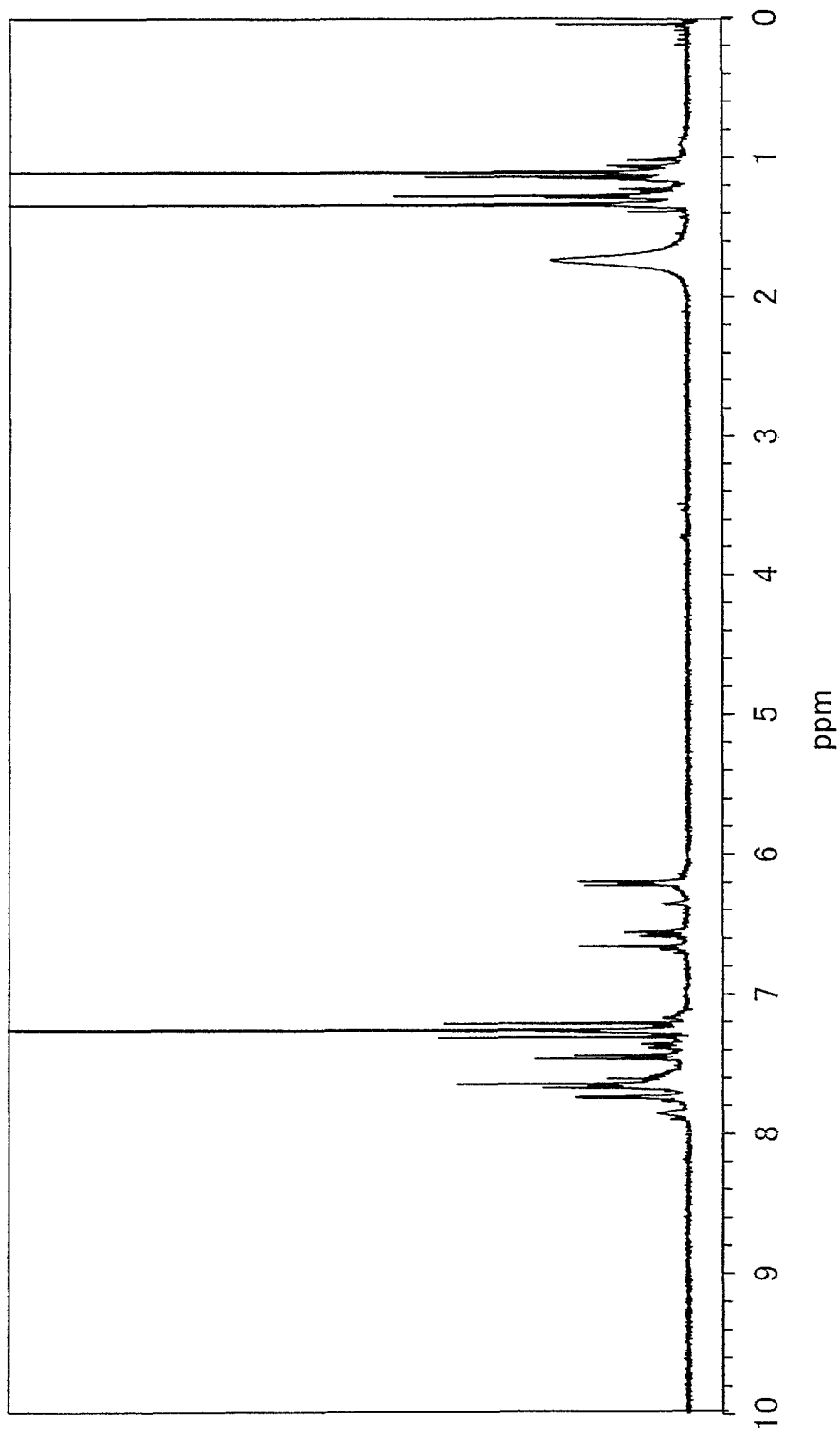
FIG. 11 is a chart obtained by analyzing an organometallic complex according to the present invention, which is synthesized in Synthesis Example 2, by $^1$H-NMR.

The obtained yellow powder was analyzed by nuclear magnetic resonance spectroscopy ($^1$H-NMR) and the product was identified as [Ir(t-Butaz)₂(bpz₄)] represented by the structural formula (15) which is one of the organometallic complexes of the present invention. The result was as follows. In addition, FIG. 11 shows a chart of $^1$H-NMR.

$^1$H-NMR. δ (CDCl₃): 7.86 (m, 1H), 7.74 (m, 4H), 7.67-7.58 (m, 14H), 7.46 (d, 4H), 7.37 (d, 2H), 6.66 (m, 3H), 6.57 (dd, 2H), 6.35 (m, 1H), 6.22-6.19 (m, 5H), 1.34 (s, 18H), 1.08 (s, 18H).

Figure 12:
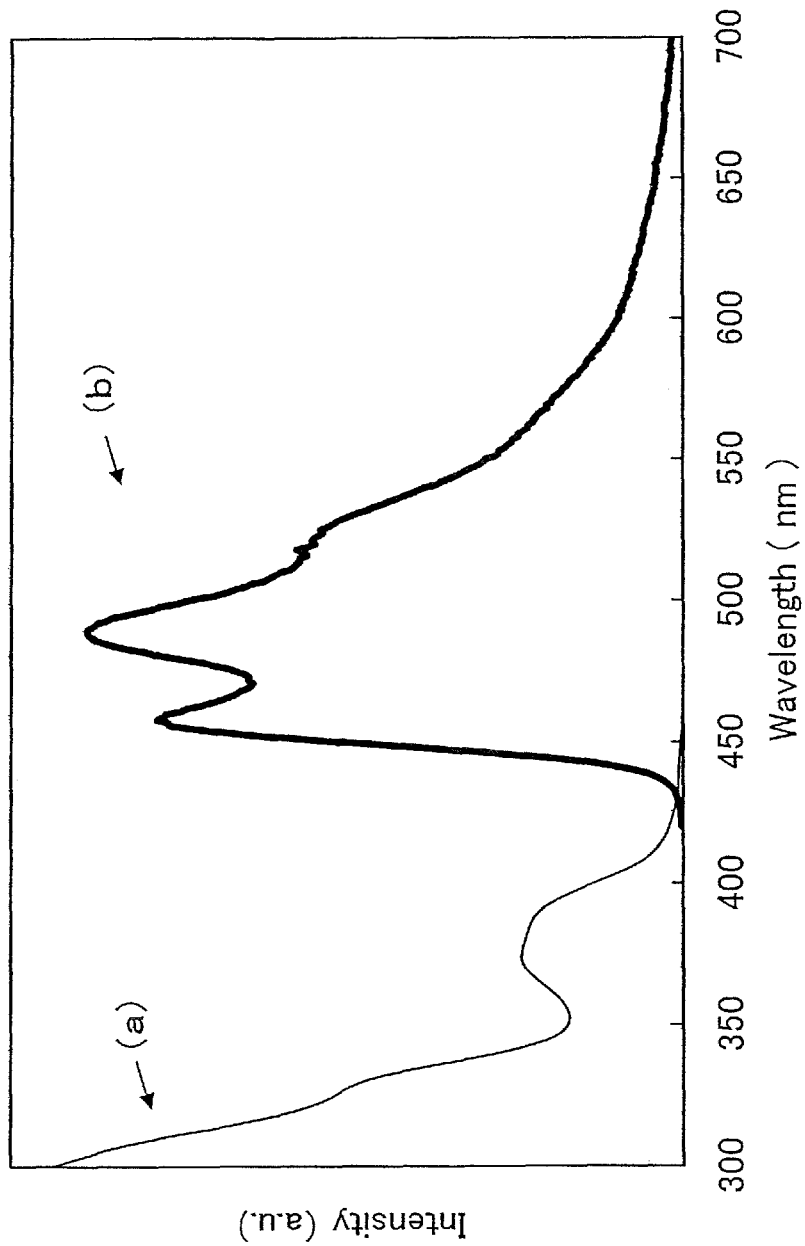
FIG. 12 is a graph showing an absorption spectrum and a light emission spectrum of an organometallic complex according to the present invention.

Moreover, FIG. 12 shows a measurement result at a room temperature of (a) an absorption spectrum and (b) an emission spectrum (PL) of Ir(t-Butaz)₂(bpz₄) in dichloromethane. In FIG. 12, the horizontal axis indicates a wavelength (nm), and the vertical axis indicates intensity of absorption and light emission (an arbitrary unit). As is apparent from FIG. 12, the organometallic complex Ir(t-Butaz)₂(bpz₄) according to the present invention has absorption peaks at 366 nm, 325 nm (sh), and 450 nm, and has emission peaks at 458 nm and 489 nm and emitted light blue light.

Synthesis Example 3

This Synthesis Example 3 will explain a synthesis method of an organometallic complex according to the present invention represented by a structural formula (55) (name: bis(2,5-diphenyl-1,3,4-oxadiazolato)(picolinato)iridium (III), abbreviation: [Ir(poda)₂(pic)]).

Step 1: Synthesis of Dinuclear Complex ([Ir(poda)₂Cl]₂)

First, 1.37 g (6.15 mmol) of 2,5-diphenyl-1,3,4-oxaziazole and 0.5 g (1.67 mmol) of iridium chloride-monohydrate were put into a 100 ml three-necked flask, and 30 ml of 2-ethoxyethanol and 10 ml of water were further added. Then, heating was performed at 100° C. for 15 hours. After reaction, 0.45 g (yield: 40%) of a yellow solid, which was the intended object, was obtained by filtering with a membrane filter. A synthetic scheme (b-1) according to the synthesis of Step 1 is shown below.

(b-1)

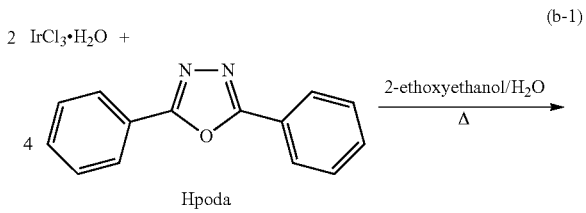

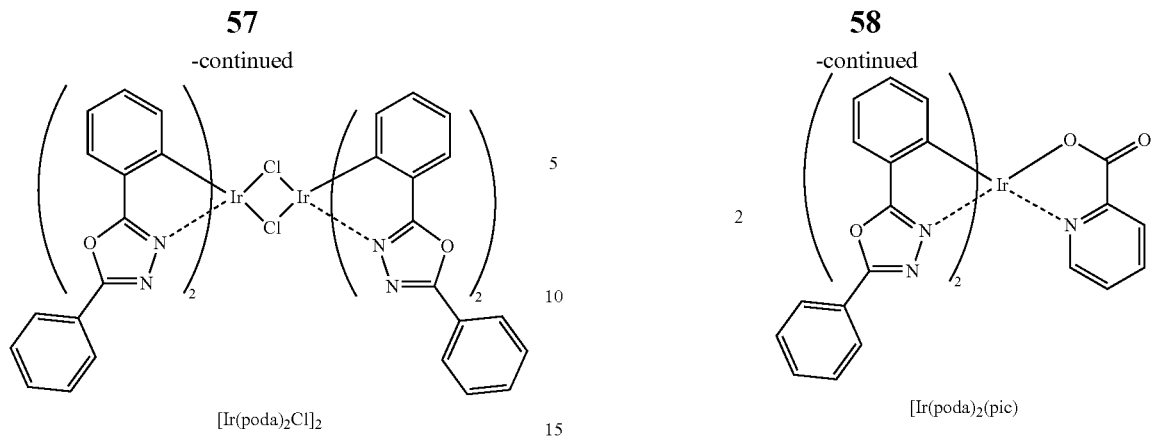

[Ir(poda)₂Cl]₂

[Ir(poda)₂(pic)]

Step 2: Synthesis of Organometallic Complex (Abbreviation: [Ir(poda)₂(Pic)]) According to the Present Invention 0.45 g (0.336 mmol) of [Ir(poda)₂Cl]₂ obtained in Step 1, 0.10 g (0.839 mmol) of picolinic acid, and 0.36 g (3.36 mmol) of sodium carbonate were put into a 100 ml three-necked flask, and 30 ml of 2-ethoxyethanol was further added. Then, heating was performed at 140° C. for 15 hours. After reaction, the solution was washed with water, a water layer was extracted with chloroform, and the obtained chloroform solution was washed along with the organic layer using saturated saline, and thereafter dried with magnesium sulfate. A substance obtained by being filtered and concentrated was purified by silica gel column chromatography (ethyl acetate) and recrystallized by chloroform and hexane. Then, 0.27 g (yield: 54%) of a yellow solid, which was the intended object, was obtained. A synthetic scheme (b-2) according to the synthesis of Step 2 is shown below.

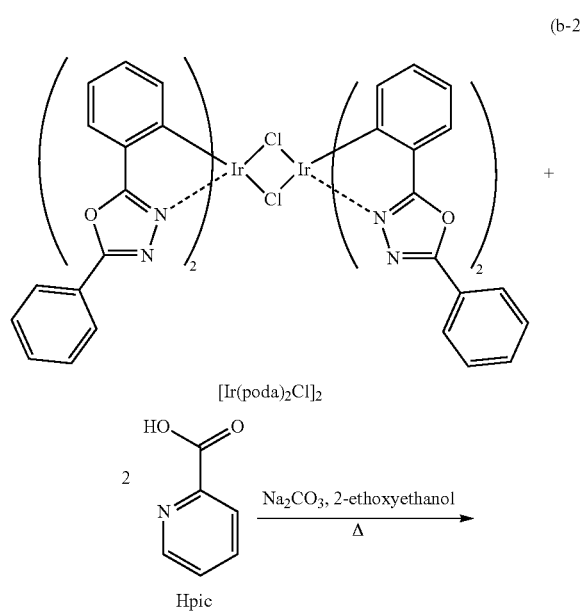

(b-2)

In addition, measurement of the thermal decomposition temperature $T_d$ of the obtained organometallic complex Ir(poda)₂(pic) according to the present invention was performed by a Thermogravimetry/Differential Thermal Analysis simultaneous measurement system (manufactured by Seiko Instruments Inc., TG/DTA-320) to find that the organometallic complex was decomposed completely at 440° C. Accordingly, it was found that the organometallic complex Ir(poda)₂(pic) according to the present invention shows favorable heat resistance.

Figure 13:
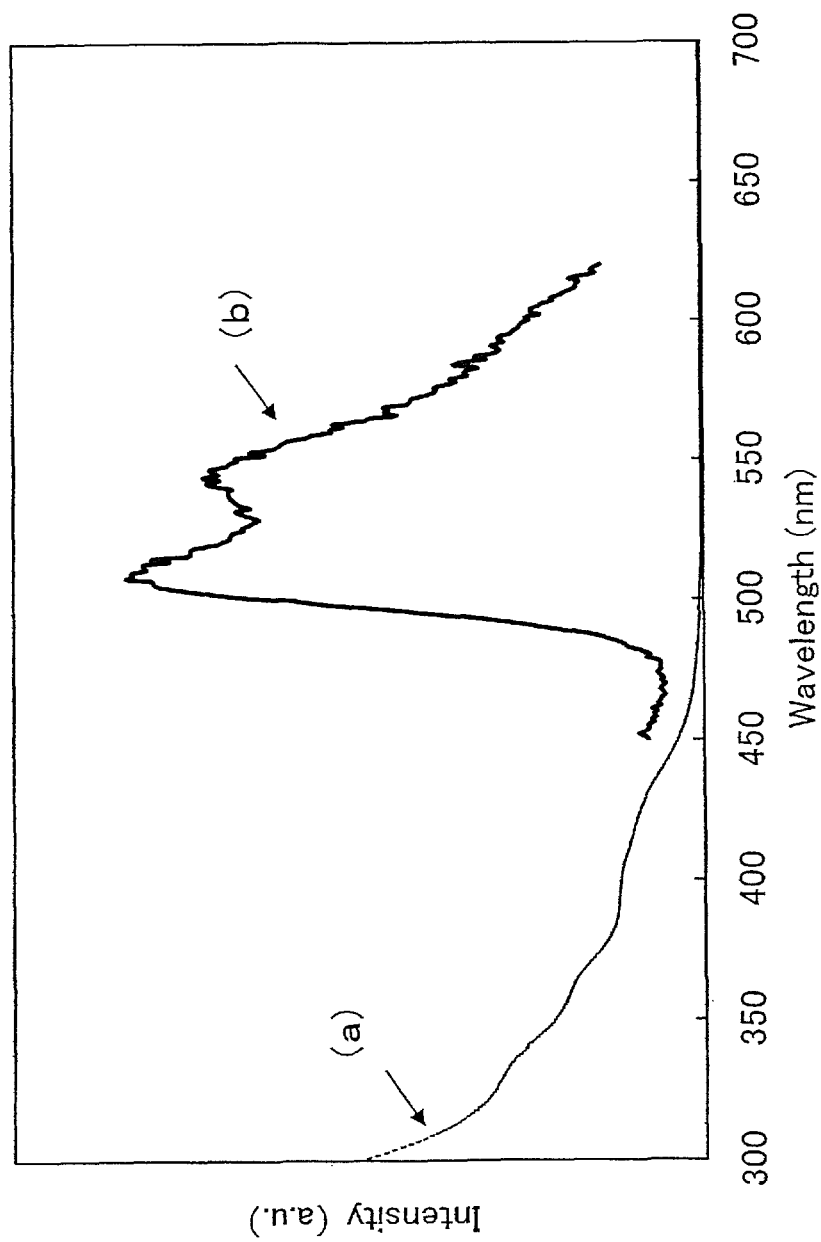
FIG. 13 is a graph showing an absorption spectrum and a light emission spectrum of an organometallic complex according to the present invention.

Moreover, FIG. 13 shows a measurement result at a room temperature of (a) an absorption spectrum and (b) an emission spectrum (PL) of Ir(poda)₂(pic) in dichloromethane. In FIG. 13, the horizontal axis indicates a wavelength (nm), and the vertical axis indicates intensity of absorption and light emission (an arbitrary unit). As is apparent from FIG. 13, the organometallic complex Ir(poda)₂(pic) according to the present invention has absorption peaks at 330 nm (sh), 360 nm (sh), 400 nm (sh), and 420 nm (sh), and has emission peak at 506 nm and emitted green light.

In addition, light emission derived from the compound is hardly observed when a dichloromethane solution of the organometallic complex Ir(poda)₂(pic) according to the present invention is irradiated with light for substituting for oxygen (oxygen substitution), while light emission is observed in a case of substituting for argon (argon substitution), thereby showing the same tendency as a substance generating phosphorescence. Accordingly, it can be confirmed that light emission derived from Ir(poda)₂(pic) is phosphorescence.

The present application is based on Japanese Patent Application serial No. 2005-303730 filed on Oct. 18, 2005 in Japanese Patent Office, the entire contents of which are hereby incorporated by reference.

What is claimed is:

1. An organometallic complex comprising a structure represented by formula (G3),

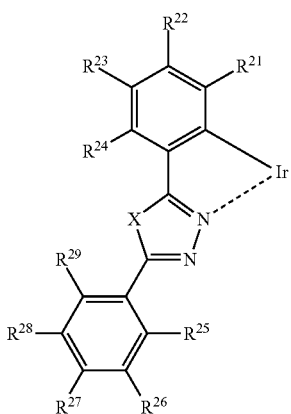

(G3)

wherein X represents —N($R^{30}$)—,
wherein $R^{30}$ represents a phenyl group having at least one electron-withdrawing substituent, and
wherein $R^{21}$ to $R^{29}$ each represent any of hydrogen, an alkyl group having 1 to 6 carbon atoms, a cycloalkyl group having 3 to 6 carbon atoms, an alkoxy group having 1 to 6 carbon atoms, an alkoxycarbonyl group having 2 to 6 carbon atoms, an acyl group having 1 to 6 carbon atoms, an acyloxy group having 1 to 6 carbon atoms, and an aryl group having 6 to 12 carbon atoms.

2. An organometallic complex comprising a structure represented by formula (G3),

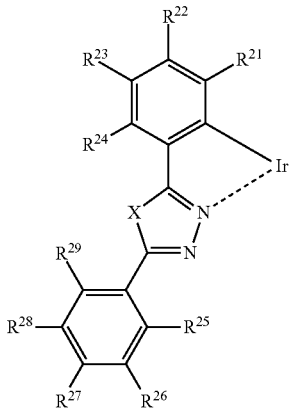

(G3)

wherein X represents —N($R^{30}$)—,
wherein $R^{30}$ represents an aryl group having 6 to 12 carbon atoms, or a heteroaryl group having 4 to 10 carbon atoms,
wherein at least one of $R^{21}$ to $R^{29}$ represents a fluorine, or a trifluoromethyl group, and
wherein the others of $R^{21}$ to $R^{29}$ each represent any of hydrogen, an alkyl group having 1 to 6 carbon atoms, a cycloalkyl group having 3 to 6 carbon atoms, an alkoxy group having 1 to 6 carbon atoms, an alkoxycarbonyl group having 2 to 6 carbon atoms, an acyl group having 1 to 6 carbon atoms, an acyloxy group having 1 to 6 carbon atoms, and an aryl group having 6 to 12 carbon atoms.

3. An organometallic complex comprising a structure represented by formula (G3), (G3)

wherein X represents —N($R^{30}$)—,
wherein $R^{30}$ represents a phenyl group having at least one electron-withdrawing substituent,
wherein at least one of $R^{21}$ to $R^{29}$ represents a fluorine, or a trifluoromethyl group, and
wherein the others of $R^{21}$ to $R^{29}$ each represent any of hydrogen, an alkyl group having 1 to 6 carbon atoms, a cycloalkyl group having 3 to 6 carbon atoms, an alkoxy group having 1 to 6 carbon atoms, an alkoxycarbonyl group having 2 to 6 carbon atoms, an acyl group having 1 to 6 carbon atoms, an acyloxy group having 1 to 6 carbon atoms, and an aryl group having 6 to 12 carbon atoms.

4. The organometallic complex according to claim 1, wherein $R^{21}$ to $R^{24}$ represent hydrogen.

5. The organometallic complex according to claim 1, wherein $R^{25}$ to $R^{29}$ represent hydrogen.

6. The organometallic complex according to claim 1, wherein the electron-withdrawing substituent is fluorine, or a trifluoromethyl group.

7. A light-emitting device using a light-emitting element as a pixel or a light source, wherein the light-emitting element includes the organometallic complex according to claim 1 between a pair of electrodes.

8. The organometallic complex according to claim 2, wherein $R^{21}$ to $R^{24}$ represent hydrogen.

9. The organometallic complex according to claim 2, wherein $R^{25}$ to $R^{29}$ represent hydrogen.

10. A light-emitting device using a light-emitting element as a pixel or a light source, wherein the light-emitting element includes the organometallic complex according to claim 2 between a pair of electrodes.

11. The organometallic complex according to claim 3, wherein $R^{21}$ to $R^{24}$ represent hydrogen.

12. The organometallic complex according to claim 3, wherein $R^{25}$ to $R^{29}$ represent hydrogen.

13. The organometallic complex according to claim 3, wherein the electron withdrawing substituent of $R^{30}$ is fluorine, or a trifluoromethyl group.

14. A light-emitting device using a light-emitting element as a pixel or a light source, wherein the light-emitting element includes the organometallic complex according to claim 3 between a pair of electrodes.

* * * * *